(12) United States Patent
Snodgrass

(10) Patent No.: US 8,143,009 B2
(45) Date of Patent: Mar. 27, 2012

(54) TOXICITY TYPING USING LIVER STEM CELLS

(75) Inventor: H. Ralph Snodgrass, San Mateo, CA (US)

(73) Assignee: VistaGen, Inc., Burlingame, CA (US)

( * ) Notice: Subject to any disclaimer, the term of this patent is extended or adjusted under 35 U.S.C. 154(b) by 708 days.

(21) Appl. No.: 11/445,733

(22) Filed: Jun. 1, 2006

(65) Prior Publication Data

US 2007/0111195 A1    May 17, 2007

Related U.S. Application Data

(63) Continuation of application No. 09/881,526, filed on Jun. 14, 2001, now abandoned.

(60) Provisional application No. 60/211,606, filed on Jun. 14, 2000.

(51) Int. Cl.
*C12Q 1/68* (2006.01)
*C12N 15/074* (2006.01)

(52) U.S. Cl. ......... 435/6.13; 435/6.1; 435/7.21; 435/7.7

(58) Field of Classification Search ........................ None
See application file for complete search history.

(56) References Cited

U.S. PATENT DOCUMENTS

| | | | |
|---|---|---|---|
| 4,153,676 A | 5/1979 | Jelinek et al. | |
| 4,569,774 A | 2/1986 | Forbus, Jr. | |
| 4,973,493 A | 11/1990 | Guire | |
| 5,002,867 A | 3/1991 | Macevicz | |
| 5,166,065 A | 11/1992 | Williams et al. | |
| 5,187,077 A | 2/1993 | Gearing et al. | |
| 5,197,985 A | 3/1993 | Caplan et al. | |
| 5,200,313 A | 4/1993 | Carrico | |
| 5,202,231 A | 4/1993 | Drmanac et al. | |
| 5,328,695 A | 7/1994 | Lucas et al. | |
| 5,486,359 A | 1/1996 | Caplan et al. | |
| 5,559,022 A | 9/1996 | Naughton et al. | |
| 5,576,207 A | 11/1996 | Reid et al. | |
| 5,645,990 A | 7/1997 | Love | |
| 5,660,986 A | 8/1997 | Harris et al. | |
| 5,670,372 A | 9/1997 | Hogan | |
| 5,686,272 A | 11/1997 | Marshall et al. | |
| 5,690,926 A | 11/1997 | Hogan | |
| 5,705,365 A | 1/1998 | Ryder et al. | |
| 5,736,332 A | 4/1998 | Mandecki | |
| 5,736,396 A | 4/1998 | Bruder et al. | |
| 5,773,213 A | 6/1998 | Gullans et al. | |
| 5,789,246 A | 8/1998 | Reid et al. | |
| 5,800,690 A | 9/1998 | Chow et al. | |
| 5,807,680 A | 9/1998 | Sutcliffe et al. | |
| 5,811,231 A | 9/1998 | Farr et al. | |
| 5,811,297 A | 9/1998 | Gopal | |
| 5,814,445 A | 9/1998 | Belyavsky et al. | |
| 5,827,735 A | 10/1998 | Young et al. | |
| 5,827,740 A | 10/1998 | Pittenger | |
| 5,861,313 A | 1/1999 | Pang et al. | |
| 6,007,993 A | 12/1999 | Wobus et al. | |
| 6,027,880 A | 2/2000 | Cronin et al. | |
| 6,033,860 A | 3/2000 | Lockhart et al. | |
| 6,040,138 A | 3/2000 | Lockhart et al. | |
| 6,069,005 A | 5/2000 | Reid et al. | |
| 6,133,436 A | 10/2000 | Köster et al. | |
| 6,171,858 B1 | 1/2001 | Holzle et al. | |
| 6,270,961 B1 | 8/2001 | Drmanac | |
| 6,299,858 B1 | 10/2001 | Serbedzija et al. | |
| 6,458,589 B1 | 10/2002 | Rambhatla et al. | |
| 6,923,959 B2 * | 8/2005 | Habener et al. | 424/93.7 |
| 7,456,017 B2 * | 11/2008 | Kubota et al. | 435/370 |
| 2001/0039006 A1 | 11/2001 | Snodgrass | |
| 2002/0012905 A1 | 1/2002 | Snodgrass | |
| 2002/0045179 A1 | 4/2002 | Snodgrass | |
| 2002/0142976 A1 * | 10/2002 | Hoekstra et al. | 514/44 |

FOREIGN PATENT DOCUMENTS

| | | |
|---|---|---|
| DE | 19606207 A1 | 8/1997 |
| EP | 0 834 575 A2 | 4/1998 |
| JP | 06-319535 A | 11/1994 |
| JP | 10-179150 A | 7/1998 |
| WO | WO-89/10977 A1 | 11/1989 |
| WO | WO-90/11548 A1 | 10/1990 |
| WO | WO-93/17126 A1 | 9/1993 |
| WO | WO-96/16162 A1 | 5/1996 |
| WO | WO-96/17958 A1 | 6/1996 |
| WO | WO-96/22362 A1 | 7/1996 |
| WO | WO-97/01644 A1 | 1/1997 |
| WO | WO-97/10365 A1 | 3/1997 |
| WO | WO-97/13877 A1 | 4/1997 |
| WO | WO-97/15690 A1 | 5/1997 |
| WO | WO-97/22720 A1 | 6/1997 |
| WO | WO-97/27317 A1 | 7/1997 |
| WO | WO-97/31256 A2 | 8/1997 |
| WO | WO-97/31256 A3 | 8/1997 |
| WO | WO-97/46313 A1 | 12/1997 |
| WO | WO-97/47734 A1 | 12/1997 |

(Continued)

OTHER PUBLICATIONS

Barany, F. (1991). "The Ligase Chain Reaction in a PCR World," *PCR Methods Appl.* 1:5-16.
Boorman, G.A. et al. (Feb. 1982). "Assessment of Myelotoxicity Caused by Environmental Chemicals," *Environmental Health Perspectives* 43:129-135.
Borer, P.N. et al. (1974). "Stability of Ribonucleic Acid Double-Stranded Helices," *J. Mol. Biol* 86:843-853.
Breslauer, K.J. et al. (Jun. 1986). "Predicting DNA Duplex Stability From the Base Sequence," *Proc. Natl. Acad. Sci. USA* 83:3746-3750.
Carninci, P. et al. (1996). "High-Efficency Full-Length cDNA Cloning by Biotinylated CAP Trapper," *Genomics* 37:327-336.

(Continued)

*Primary Examiner* — Maria Marvich
(74) *Attorney, Agent, or Firm* — Morrison & Foerster LLP

(57) ABSTRACT

This invention provides methods and systems for identifying and typing toxicity of chemical compositions, as well as for screening new compositions for toxicity. The invention involves detecting alterations in gene or protein expression and hence establishing molecular profiles in isolated mammalian LSCs contacted with various chemical compositions of known and unknown toxicities, and correlating the molecular profiles with toxicities of the chemical compositions.

27 Claims, 4 Drawing Sheets

FOREIGN PATENT DOCUMENTS

| WO | WO-98/07841 A1 | 2/1998 |
| --- | --- | --- |
| WO | WO-98/12354 A1 | 3/1998 |
| WO | WO-98/26098 A1 | 6/1998 |
| WO | WO-98/26098 C1 | 6/1998 |
| WO | WO-99/10535 A1 | 3/1999 |
| WO | WO-99/23254 A1 | 5/1999 |
| WO | WO-99/27090 A1 | 6/1999 |
| WO | WO-99/44062 A1 | 9/1999 |
| WO | WO-00/29002 A2 | 5/2000 |
| WO | WO-00/29002 A3 | 5/2000 |
| WO | WO-00/34525 A1 | 6/2000 |
| WO | WO-00/34525 C1 | 6/2000 |
| WO | WO-01/96865 A1 | 12/2001 |
| WO | WO-01/96866 A1 | 12/2001 |

OTHER PUBLICATIONS

Chenchik, A. et al. (Sep. 1996). "Full-Length cDNA Cloning and Determination of mRNA 5' and 3' Ends by Amplification of Adaptor-Ligated cDNA," *Biotechniques* 21(3):526-534.

Church, G.M. et al. (Apr. 1984). "Genomic Sequencing," *Proc. Natl. Acad. Sci. USA* 81(7):1991-1995.

Coghlan, A. (Oct. 25, 1997). "Running on Parallel Lines," *New Scientist* pp. 18.

Craig, J.C. et al. (1996). "Screening for Reproductive Toxicty in *Fundulus heteroclitus* by Genetic Expression Profiling," *Biomarkers* 1(2):123-135.

Damha, M.J. et al. (1990). "An Improved Procedure for Derivatization of Controlled-Pore Glass Beads for Solid-Phase Oligonucleotide Synthesis," *Nucleic Acids Research* 18(13):3813-3821.

Denhardt, D.T. (1966). "A Membrane-Filter Technique for the Detection of Complementary DNA," *Biochem. and Biophys. Res. Comm.* 23(5):641-646.

Gillespie, D. et al. (1965). "A Quantitative Assay for DNA-RNA Hybrids With DNA Immobilized on a Membrane," *J. Mol. Biol.* 12(3):829-842.

Hakvoort, T.B.M. et al. (1996). "Preparation of a Differentially Expressed, Full-Length cDNA Expression Library by RecA-Mediated Triple-Strand Formation With Subtractively Enriched cDNA Fragments," *Nucleic Acids Research* 24(17):3478-3480.

Hamadeh, H.K. et al. (2002). "Prediction of Compound Signature Using Density Gene Expression Profiling," *Toxicological Sciences* 67:232-240.

Hillier, L. et al. (Nov. 1991). "OSP: A Computer Program for Choosing PCR and DNA Sequencing Primers," *PCR Methods and Applications* 1(2):124-128.

Innis, M.A. et al. (1990). "Optimization of PCRs," Chapter 1 in *PCR Protocols: A Guide to Methods and Applications*, Innis, M.A. et al., eds., Academic Press, inc.: San Diego, CA, pp. 3-12.

Jacobs, K.A. et al. (1988). "The Thermal Stability of Oligonucleotide Duplexes is Sequence Independent in Tetraalkylammonium Salt Solutions: Application to Identifying Recombinant DNA Clones," *Nucleic Acids Research* 16(10):4637-4650.

Lillie, J. (Jul./Aug. 1997). "Probing the Genome for New Drugs and Targets with DNA Arrays," *Drug Development Research* 41(3/4):160-172.

Lo, V.-M. D. et al. (1990). "Incorporation of Biotinylated dUTP," Chapter 14 in *PCR Protocols: A Guide to Methods and Applications*, Innis, M.A. et al., eds., Academic Press, Inc.: San Diego, CA, pp. 113-118.

Marshall, A. et al. (Jan. 1998). "DNA Chips: An Array of Possibilities," *Nature Biotechnology* 16:27-31.

Pearson, W.R. (1990). "Rapid and Sensitive Sequence Comparison With FASTP and FASTA," Chapter 5 in *Methods in Enzymology*, Academic Press, Inc. 183(5):63-98.

Pearson, W.R. et al. (Apr. 1988). "Improved Tools for Biological Sequence Comparison," *Proc. Natl. Acad. Sci. USA* 85(8):2444-2448.

Pon, R.T. et al. (1988). "Derivatization of Controlled Pore Glass Beads for Solid Phase Oligonucleotide Synthesis," *BioTechniques* 6(8):768-775.

Rychlik, W. et al. (1990). "Optimization of the Annealing Temperature for DNA Amplification In Vitro," *Nucleic Acids Research* 18(21):6409-6412.

Schmitt, R.M. et al. (1991). "Hematopoietic Development of Embryonic Stem Cells in Vitro: Cytokine and Receptor Gene Expression," *Genes and Development* 5(5):728-740.

Shirozu, M. et al. (1996). "Characterization of Novel Secreted and Membrane Proteins Isolated by the Signal Sequence Trap Method," *Genomics* 37(3):273-280.

Shoemaker, D.D. et al. (Dec. 1996). "Quantitative Phenotypic Analysis of Yeast Deletion Mutants Using a Highly Parallel Molecular Bar-Coding Strategy," *Nature Genetics* 14(4):450-456.

Tijssen, P. (1993). "Hybridization with Nucleic Acid Probes," Chapter 2 in *Laboratory Techniques in Biochemistry and Molecular Biology*, Van der Vliet, P.C., ed., Elsevier: Amsterdam, 24:19-78.

Volkmuth, W.D. et al. (Aug. 13, 1992). "DNA Electrophoresis in Microlithographic Arrays," *Nature* 358(6387):600-602.

Wobus, A.M. et al. (1994). "In Vitro Differentiation of Embryonic Stem Cells into Cardiomyocytes or Skeletal Muscle Cells is Specifically Modulated by Retinoic Acid," *Roux's Arch. Dev. Biol.* 204(1):36-45.

Barany. (1991). "Genetic Disease Detection and DNA Amplification Using Cloned Thermostable Ligase," *Proc. Natl. Acad. Sci. USA* 88:189-193.

Becker, S. et al. (1992). "Localization of Endoderm-Specific mRNAs in Differentiating F9 Embryoid Bodies," *Mech. Dev.*37:3-12.

Bichet, S. et al. (1999). "Oxygen Tension Modulates β-Globin Switching in Embroid Bodies", *FASEB J.* 13:285-295.

Bielinska, M. (1997). "Induction of Yolk Sac Endoderm in GATA-4-Deficient Embryoid Bodies by Retinoic Acid," *Mech. Dev.*65:43-54.

Blouin et al. (1992). "Cytokeratin 14 Expression in Rat Liver Cells I Culture and Localization in vivo," *Differentiation* 52:45-54.

Brill et al. (1994). "Extracellular Matrix Regulation of Growth and Gene Expression in Liver Cell Lineages and Hepatomas" in *The Liver Biology and Pathobiology* pp. 869-897. (Arias et al., Third Edition, Raven Press, NY).

Brill et al. (1995). "Maturation-Dependent Changes in the Regulation of Liver-Specific Gene Expression in Embryonal Versus Adult Primary Liver Cultures," *Differentiation* 59:95-102.

Brill et al. (1999). "Expansion Conditions for Early Hepatic Progenitor Cells from Embryonal and Neonatal Rat Livers," *Digestive Diseases & Sciences* 44:364-371.

Bruchez et al. (1998). "Semiconductor Nanocrystals as Fluorescent Biological Labels," *Science* 281 :2013-2016.

Carere et al. (2002). "In Vitro Toxicology Methods: Impact on Regulation form Technical and Scientific Advancements," *Toxicol. Lett.* 127(1-3):153-160.

Chan et al. (1998). "Quantum Dot Bioconjugates for Ultrasensitive Nonisotopic Detection," *Science* 281 :2016-2018.

Church et al. (1999). "Different Effects of BMP Antagonists Noggin & Fetuin on the Osteogenic Differentiation of Human Marrow," *Calcified Tissue International* 64(1):S54.

Communication Pursuant to Article 115(2) EPC. (Jan. 15, 2002). Observations filed by a third party concerning the pantentability of the invention.

Davila et al. (1998). "Predictive Value of in Vitro Model System in Toxicology," *Annu Rev. Pharmacol Toxico*l. 38:63-96.

Doetschman et al. (1985). "The In Vitro Development of Blastocyst-Derived Embryonic Stem Cell Lines: Formation of Visceral Yolk Sac, Blood Islands and Myocardium," *J. Embryol. Exp. Morph*. 87:27-45.

Duncan, W.A. (1967). "Species Variation in Drug Metabolism", *Advancement of Science* 23(116):537-541.

Fiorino et al. (1998). "Maturation-Dependent Gene Expression in a Conditionally Transformed Liver Progenitor Cell Line," *In Vitro Cell. Dev. Biol.—Animal* 34:247-258.

Flint. (1998). "Predicting In Vivo Toxicity," *Toxicology in Vitro* 12:591-595.

Gajovi'c, S. (1998). "Genes Expressed After Retinoic Acid-Mediated Differentiation of Embryoid Bodies are Likely to be Expressed During Embryo Development," *Exp. Cell. Res.* 242:138-143.

Gall et al. (1990). "Development of Intrahepatic Bile Ducts in Rat Foetal Liver Explants in vitro," *J. Exp. Pathol.* 71:41-50.

Garcia-Sanz, M.(1996). "Multiparametic Analysis of Cell Differentiation in Teratocarcinoma Embryoid Bodies," *Int. J. Dev. Biol.I* , Proceedings of the first congress of the Spanish society of developmental biology and international workshop on developmental approaches in cancer biology, Leioa, Spain, 279S-280S.

Germain et al. (1988). "Biliary Epithelial and Hepatocytic Cell Lineage Relationships in Embryonic Rat Liver as Determined by the Differential Expression of Cytokeratins, I-Fetoprotein, Albumin, and Cell Surface-expposed Components," *Cancer Res.* 48:4909-4918.

Ghiglione, C. et al. (1996). "Early Gene Expression Along the Animal-Vegetal Axis in Sea Urchin Embryoids and Grafted Embryos," *Development* 122:3067-3074.

Gray, N.S. et al. (1998). "Exploiting Chemical Libraries, Structure, and Genomics in the Search for Kinase Inhibitors," *Science* 281:533-538.

Grisham et al. (1997). "Liver Stem Cells" In *Stem Cells* Academic Press: London, pp. 233-282.

Harlow et al., eds. (1988). *Antibodies: A Laboratory Manual.* Cold Spring Harbor Laboratory Press: Cold Spring Harbor, NY., pp. iii-ix (Table of Contents).

Hogan et al., eds. (1986). *Manipulating the Mouse Embryo: A Laboratory Manual.* Cold Spring Harbor Laboratory Press: Cold Spring Harbor, NY., pp. vii-ix (Table of Contents).

Innis et al., eds. (1990). *PCR Protocols: A Guide to Methods and Applications.* Academic Press, Inc.: San Diego, CA., pp. v-x (Table of Contents).

Ji et al. (2000). "Patterns of Gene Expression Associated with BMP-2-Induced Osteoblast and Adipocyte Differentiation of Mesenchymal Progenitor Cell 3T3-F442A," *J Bone Miner Metab.* 18(3):132-139.

Keller et al. (1993). "Hematopoietic Commitment During Embryonic Stem Cell Differentiation in Culture," *Mol. Cell. Biol.* 13:473-486.

Klaassen et al., eds. (1996). *Casarett and Doull's Toxicology: The Basic Science of Poisons.* 5th Edition, McGraw-Hill: New York, NY., pp. v-vii (Table of Contents).

Krah, K. et al. (1994). "Induction of Vasculogenesis in Quail Blastodisc-Derived Embryoid Bodies," *Dev Biol.* 164:123-132.

Kyuwa, S. et al. (1997). "Characterization of Embryonic Stem-Like Cell Lines Derived From Embryoid Bodies," *Exp. Anim.* 46(1):11-16.

Landegren et al. (1988). "A Ligase-Mediated Gene Detection Technique," *Science* 241:1077-1080.

Leahy, A. et al. (1999). "Use of Developmental Marker Genes to Define Temporal and Spatial Patterns of Differentiation During Embryoid Body Formation," *J. Exp. Zool.* 284:67-81.

Levenson et al. (1990). "Nonisotopically Labeled Probes and Primers," In *PCR Protocols: A Guide to Methods and Applications.* Innis et al. eds., Academic Press, Inc.: San Diego, CA., pp. 99-112.

Ling et al. (1997). "In Vitro Differentiation of Embryonic Stem Cells: Immunophentypic Analysis of Cultured Embryoid Bodies," *J. Cell. Physiology* 171:104-115.

Ling, V. et al. (1998). "Embryonic Stem Cells and Embryoid Bodies Express Lymphocyte Costimulatory Molecules," *J. Cell. Physiol.* 241:55-65.

Maier, E. et al. (1997). "Automated Array Technologies for Gene Expression Profiling," *Drug Discovery Today* 2(8):315-324.

Maier, P. (1988). "Development of In Vitro Toxicity Tests with Cultures of Freshly Isolated Rat Hepatocytes," *Experientia* 44(10):807-817.

Marceau. (1990). "Biology of Disease: Cell Lineages and Differentiation Programs in Epidermal, Urothelial and Hepatic Tissues and Their Neoplasms," *Lab. Invest.* 63:4-20.

Marshall. (Nov. 6, 1998). "A Versatile Cell Line Raises Scientific Hopes, Legal Questions," *Science* 282:1014-1015.

Matsui et al. (1992). "Derivation of Plunpotential Embryonic Stem Cells from Murine Primordial Germ Cells in Culture," *Department of Cell Biology* 70:841-847.

McCormick et al. (1997). "Microchannel Electrophoretic Separations of DNA in Injection-Molded Plastic Substrates," *Anal. Chem.* 69:2626-2630.

Moll et al. (1982). "The Catalog of Human Cytokeratins: Patterns of Expression in Normal Epithelia, Tumors and Cultured Cells," *Cell* 31:11-24.

Monzo, M. et al. (1992). "Effect of Ascitic Liquid on Growth in vitro of Embryoid Bodies Derived From Teratocarcinoma," *Histol. Histopathol.* 7:23-27.

Morini, M. et al. (1999). "Localization and Expression of Integrin Subunits in the Embryoid Bodies of F9 Teracarcinoma Cells," *Exp. Cell. Res.* 247:114-122.

Osborn et al.(1982). "Intermediate Filaments: Cell-type-specific Markers in Differentiation and Pathology," *Cell* 31:303-306.

Park, J.I. et al. (1998). "Differentiative Potential of a Mouse Parthenogenetic Embryonic Stem Cell Line Revealed by Embryoid Body Formation in vitro," *Jpn. J. Vet. Res.* 46(1):19-28.

Pittenger et al. (1999). "Multilineage Potential of Adult Human Mesenchymal Stem Cells," *Science* 284:143-147.

Reid (1997). "Chapter 31 : Stem Cell/Lineage Biology and Lineage-Dependent Extracellular Matrix Chemistry: Keys to Tissue Engineering of Quiescent Tissues such as Liver," Principles of Tissue Engineering (R.P. Lanza/Academic Press, Austin TX), pp. 481-514.

Reid et al.(1997). "Ex vivo Maintenance of Differenteiated Mammalian Cells," *Basic Cell Culture Protocols* 75:31-57. (Humana Press, Totwa, NJ).

Robertson. (1987). "Embryo-Derived Stem Cell Lines," Chapter 4 In *Teratocarcinomas and Embryonic Stem Cells: A Practical Approach.* Robertson, E., ed., IRL Press: Washington, DC., pp. 71-112.

Robertson et al. (1986). "Germ-Line Transmission of Genes Introduced into Cultured Pluripotential Cells by Retroviral Vector," *Nature* 323:445-448.

Sambrook et al., eds. (1989). *Molecular Cloning, A Laboratory Manual.* 2nd ed., Cold Spring Harbor Laboratory Press: Cold Spring Harbor, NY., pp. xi-xxxviii (Table of Contents).

Sanchez A. et al. (1991). "Myosin Heavy Chain Gene Expression in Mouse Embryoid Bodies," *J. Biol. Chem.* 266(33):22419-22426.

Schmitt et al. (1991). "Hematopoietic Development of Embryonic Stem Cells In Vitro: Cytokine and Receptor Gene Expression," *Genes Dev.* 5:728-740.

Seamark. (1994). "Progress and Emerging Problems in Livestock Transgenesis: a Summary Perspective," *Reprod. Fertil. Dev.* 6:653-657.

Service. (1998). "Microchip Arrays Put DNA on the Spot," *Science* 282:396-399.

Shalon et al. (1996). "A DNA Microarray System for Analyzing Complex DNA Samples Using Two-Color Fluorescent Probe Hybridization," *Genome Res.* 6:639-645.

Shamblott et al. (1998). "Derivation of Pluripotent Stem Cells from Cultured Human Primordial Germ Cells," *Proc Natl Acad Sci USA* 95:13726-13731.

Shim et al. (1997). "Isolation of Pluripotent Stem Cells from Cultured Porcine Primordial Germ Cells," *Biol. Reprod.* 57:1089-1095.

Shiojiri et al. (1991). "Cell Lineages and Oval Cell Progenitors in Rat Liver Development," *Cancer Res.* 51:2611-2620.

Shiojiri et al.(1993). "Differentiation of Functional Hepatocytes and Biliary Epithelial Cells From Immature Hepatocytes of the Fetal Mouse in vitro," *Anat. Embryol* 187:221-229.

Snodgrass et al. (1993). "Embryonic Stem Cells: Research and Clinical Potentials," In *Peripheral Blood Stem Cells.* Smith et al. eds., American Association of Blood Banks: Bethesda, MD., pp. 65-83.

Spielmann et al. (1997). "The Ebryonic Stem Cell Test, an in Vitro Embyotoxicity Test Using Two Permanent Mouse Cell Lines: 3T3 Fibroblasts and Embryonic Stem Cells," *In Vitro Toxicology* 10(1):119-127.

Thomas et al. (2003). *Toxicogenomics,*. Editors: Inoue and Pennie, Springer-Verlag Tokyo: Tokyo Japan. pp. 31-38.

Thomson et al. (1996). "Pluripotent Cell Lines Derived from Common Marmoset (*Callithrix jacchus*) Blastocytes," *Biol. Reprod.* 55:254-259.

Thomson et al. (1998). "Embryonic Stem Cell Lines Derived from Human Blastocysts," *Science* 282:1145-1147.

Thomson et al. (1998). "Primate Embryonic Stem Cells," Chapter 4, vol. 38 In *Current Topics in Developmental Biology.* Pedersen et al. eds., Academic Press: San Diego, CA., pp. 133-165.

Todaro et al. (1963). "Quantitative Studies of the Growth of Mouse Embryo Cells in Culture and Their Development Into Established Lines," *J. Cell. Biol.* 17:299-313.

Tugwood et al (2003). "Genomics and the Search for Novel Biomarkers in Toxicology," *Biomarkers* 8(2):79-82.

Unda, F.J. et al. (1994). "Co-Expression of Laminin and a 67 kDa Laminin-Binding Protein in Teratocarcinoma Embryoid Bodies," *Int J. Dev. Biol.* 38:121-126.

Velculescu et al. (1995). "Serial Analysis of Gene Expression," *Science* 270:484-487.

Wang, R (1992) "Embryonic stem cell-derived cystic embryoid bodies form vascular channels: an in vitro model of blood vessel development" *Development* 114:303-316.

Ware et al. (1972). "Inherited Resistance to N- and B-Tropic Murine Leukemia Viruses in Vitro: Evidence That Congenic Mouse Strains SIM and SIM.R Differ at the Fv-1 Locus," *Virology* 50:339-348.

Waring et al. (2002). "The Promise of Toxicogenomics," *Cur. Opin. Mol. Ther.* 4(3):229-235.

Wartenberg, M. et al. (1998) "The Embryoid Body as a Novel in vitro Assay System for Antigiogenic Agents," *Lab Invest* 78(10):1301-1314.

Williams. (1978). "Species Variations in the Pathways of Drug Metabolism," *Environ. Health Perspect.* 22:133-138.

Wu et al. (1989). "The Ligation Amplification Reaction (LAR)—Amplification of Specific DNA Sequences Using Sequential Rounds of Template-Dependent Ligation," *Genomics* 4:560-569.

Xiong, J.W. et al. (1998) "Large-Scale Screening for Developmental Genes in Embryonic Stem Cells and Embryonic Bodies using Retroviral Entrapment Vectors," *Dev. Dyn.* 212:181-197.

Yamada, G. et al. (1994). "Regulated Expression of Brachyury(T), NKX1.1 and Pax Genes in Embryoid Bodies," *Biochem Biophys Res Commun* 199(2):552-563.

Young, H.E. et al. (1988). "Initial Characterization of Small Proteoglycans Synthesized by Embryonic Chick Leg Muscle-Associated Connective Tissues," *Connective Tissue Research* 17:99-118.

Young, H.E. et al. (1991). "Cryopreservation of Embryonic Chick Myogenic Lineage-Committed Stem Cells," *J. Tiss. Cult. Meth.* 13:275-283.

Young, H.E. et al. (1992). "Isolation of Embryonic Chick Myosatellite and Pluripotent Stem Cells," *J. Tiss. Cult. Method* 14:85-92.

Young, H.E. et al. (1999). "Human Pluripotent and Progenitor Cells Display Cell Surface Cluster Differentiation Markers CD10, CD13, CD56, and MHC Class-I (443385)," *Proc. Soc. Exp. Biol. Med.* 221:63-71.

Zhang et al. (1997). "Gene Expression Profiles in Normal and Cancer Cells," *Science* 276:1268-1272.

\* cited by examiner

TOXICITY TYPING USING LIVER STEM CELLS

CROSS-REFERENCE TO RELATED APPLICATIONS

This application is a continuation of U.S. patent application Ser. No. 09/881,526, filed on Jun. 14, 2001, now abandoned, which claims the priority benefit of the provisional patent application U.S. Ser. No. 60/211,606, filed Jun. 14, 2000, which is hereby incorporated by reference in its entirety.

TECHNICAL FIELD

This invention provides methods for identifying and characterizing toxic compounds as well as for screening new compounds for toxic effects.

BACKGROUND ART

Advances in methods of modern drug discovery such as those utilizing high throughput screening assays of combinatorial chemical libraries continue to provide us with unprecedented numbers of drug candidates for treatment of diseases. However, the problem of drug toxicity to the host system continues to be a significant rate-limiting step in the translation of drug candidates from the laboratory to the healthcare setting. Similar toxicity problems hinder the development of industrial and household chemicals as well. Besides being expensive and time-consuming, currently available toxicological screening assays fail to detect all toxicities associated with human therapy. For instance, as much as one third of all prospective human therapeutics fail in the first phase of human clinical trials because of unexpected toxicity. Better means of screening potential therapeutics for potential toxicity would reduce the cost and uncertainty of developing new therapeutics and, by reducing uncertainty, would encourage the private sector to commit additional resources to drug development.

Currently available alternatives to traditional "single-reporter" cell lines and animal toxicity testing do not fully meet these needs. For example, Farr, U.S. Pat. No. 5,811,231, provides methods of identifying and characterizing toxic compounds by choosing selected stress promoters and determining the level of the transcription of genes linked to these promoters in cells of various cell lines. This method therefore depends on the degree to which both the promoter and the cell lines are representative of the effect of the potentially toxic agent on the organism of interest.

The use of hybridization arrays of oligonucleotides provides another route for determining the potential toxicity of chemical compositions. Exposing cells of a culture to a chemical composition and then comparing the expression pattern of the exposed cells to that of cells exposed to other chemical agents permits one to detect patterns of expression similar to that of the test compound, and thus to predict that the toxicities of the chemical compositions will be similar. See, e.g., Service, R., *Science* (1998), 282:396-399. These methods suffer from the fact that individual cell lines may not be fully representative of the complex biology of an intact organism. Moreover, even repeating the tests in multiple cell lines does not reproduce or account for the complex interactions among cells and tissues that occur in an organism.

Liver cell-based toxicity assays are also known. For example, Maier describes development of an in vitro toxicity test with cultures of freshly isolated rat hepatocytes. Maier, P., *Experientia* (1988), 44(10):807-817. This test is based on drug-induced pathological alterations in ploidy in hepatocytes as indicators of compounds which interfere with cell differentiation in liver. Sawai and Awata describe a method for culturing liver cells that can be used for testing the toxicity of test substances. Sawai and Awata, Japanese Patent 10179150. Takashina and Naoki describe established subculturable hepatic cells obtained by fusing a subculturable hepatic cell strain to a hepatocyte that can be used for toxicity tests. Takashina and Naoki, Japanese Patent 06319535. Again, toxicity assays using cell lines such as these may not fully take into account the complex biology of an intact organism or tissue, and cannot address the contributions of cell and tissue interactions in determining toxicity effects.

Lockhart et al. describe a method of screening a drug for deleterious side effects on a cell using expression profiles of a group of known genes. Lockhart et al., U.S. Pat. No. 6,033,860. This method assesses alterations in expression of 16 known genes, and therefore is limited to only drug and toxicity types that alter the expression of a very small number of genes whose identity is known and expression level can be specifically measured.

A method for identifying or testing cytotoxicity of an agent based on expression of cytochrome P450 is also known. Harris et al., U.S. Pat. No. 5,660,986. This method is based on testing cytotoxicity of agents on human bronchial and liver epithelial cell lines expressing exogenous cytochrome P450. This method is limited by its narrow focus on the expression of a particular gene and its nature as an assay that is based on cell lines that do not take account of complex cell and tissue interactions.

Largely because it performs a vital role in detoxifying poisonous substances in the body, the liver is the site wherein the toxicity effects of substances are most frequently and severely manifested. See, e.g., Table 1. Therefore, toxicity assays that focus primarily on the effects of potentially toxic compounds on cells related to or found in the liver would be expected to be particularly informative.

What is needed in the art is a method of systematically testing chemical compositions for potential toxicity in a milieu in which cells interact with cells of other types and that is most relevant to the common target(s) of toxic effects. What is further needed is a means of doing so which is relevant to the effect of the composition on whole organisms or tissues, without the cost, time, and ethical ramification of animal and human testing. The present invention addresses these and other needs.

DISCLOSURE OF THE INVENTION

This invention provides novel methods for assessing the toxicity of chemical compositions. In one group of embodiments, the invention is directed to methods of creating a molecular profile of a chemical composition, comprising the steps of a) contacting an isolated population of mammalian liver stem cells (LSCs) with the chemical composition; and b) recording alterations in gene expression or protein expression in the mammalian LSCs in response to the chemical composition to create a molecular profile of the chemical composition.

The invention further embodies methods of compiling a library of molecular profiles of chemical compositions having predetermined toxicities, comprising the steps of a) contacting an isolated population of mammalian LSCs with a chemical composition having predetermined toxicities; b) recording alterations in gene expression or protein expression in the mammalian LSCs in response to the chemical composition to create a molecular profile of the chemical composition; and c) compiling a library of molecular profiles by repeating steps a) and b) with at least two chemical compositions having predetermined toxicities. Libraries of molecular profiles compiled by methods of the invention can be stored in suitable storage devices, such as computer hard drives, compact disks, cassettes, floppy disks and the like. Generally and preferably, suitable storage devices store such data in machine (such as computer) readable form.

Another embodiment of the present invention provides methods for typing toxicity of a test chemical composition by comparing its molecular profile in LSCs with that of an identified chemical composition with predetermined toxicity. In one aspect, the test chemical composition can be the same as the chemical composition having predetermined toxicities. For example, the test chemical is identified through this testing as exhibiting the identical molecular profile as the known chemical composition.

The invention further encompasses systemic methods for typing the toxicity of a test chemical composition by making the profile comparison with a library comprising profiles of multiple chemical compositions with predetermined toxicities. Preferably, the chemical compositions comprised in a library exert similar toxicities in terms of types and target tissues or organs. The library can be in the form of a database. A database may comprise more than one library for chemical compositions of different toxicity categories.

In one aspect of the present invention, the toxicity of a test chemical composition can be ranked according to a comparison of its molecular profile in LSCs to those of chemical compositions with predetermined toxicities.

LSCs in the present invention can be of human or non-human mammals, including those of murine species, as well as canine, feline, porcine, bovine, caprine, equine, and sheep species.

The alterations in levels of gene or protein expression can be detected by use of a label selected from any of the following: fluorescent, calorimetric, radioactive, enzyme, enzyme substrate, nucleoside analog, magnetic, glass, or latex bead, colloidal gold, and electronic transponder. The alterations can also be detected by mass spectrometry. The chemical composition can be known (for example, a potential new drug) or unknown (for example, a sample of an unknown chemical found dumped near a roadside and of unknown toxicity).

Further, the chemical compositions can be therapeutic agents (or potential therapeutic agents), or agents of known toxicities, such as neurotoxins, hepatic toxins, toxins of hematopoietic cells, myotoxins, carcinogens, teratogens, or toxins to one or more reproductive organs. The chemical compositions can further be agricultural chemicals, such as pesticides, fungicides, nematicides, and fertilizers, cosmetics, including so-called "cosmeceuticals," industrial wastes or by-products, or environmental contaminants. They can also be animal therapeutics or potential animal therapeutics.

The invention also provides LSCs provided in array format (for example, liquid arrays) that can be conveniently used for conducting methods of the invention. Cells provided in array format can be exposed to chemical compositions of interest, and the molecular profiles of the cells determined. The molecular profiles can be determined by, for example, probing the LSCs on the substrate (of the array) itself, or by detaching cells from the substrate (of the array) and preparing them for determination of molecular profiles as described herein.

The invention further includes integrated systems for comparing the molecular profile of a chemical composition to a library of molecular profiles of chemical compositions, comprising an array reader adapted to read the pattern of labels on an array, operably linked to a computer comprising a data file having a plurality of gene expression or protein expression profiles of mammalian LSCs contacted with known or unknown chemical compositions.

The invention also includes integrated systems for correlating the molecular profile and toxicity of a chemical composition comprising an array reader adapted to read the pattern of labels on an array, operably linked to a digital computer comprising a database file having a plurality of molecular profiles of mammalian LSCs contacted with chemical compositions with predetermined toxicities and a program suitable for molecular profile-toxicity correlation. The integrated systems of the invention can be capable of reading more than 500 labels in an hour, and further can be operably linked to an optical detector for reading the pattern of labels on an array.

BRIEF DESCRIPTION OF THE DRAWINGS

FIG. 1A illustrates a half-tone reproduction of a readout from a mass spectrometer. The top band is the mass spectrum for control LSCs, which are grown in the absence of either of the test chemical compositions. The middle band is the mass spectrum for the LSCs grown in the presence of a test chemical composition (test composition I), and the bottom band of FIG. 1A shows the mass spectrum of nuclear proteins expressed by LSCs exposed to a second test chemical composition (test composition II).

FIGS. 1B and 1C are bar graphs that illustrate computational subtractions of identical proteins between the respective test LSCs and the control LSCs to indicate only those proteins which are significantly different in expression between the test and the control LSCs. Each bar represents a single protein and the height of the bar represents the amount of protein expressed by the LSCs exposed to the test composition compared to the amount expressed by LSCs not exposed to the chemical composition. FIG. 1B: protein expression of test LSCs contacted with test composition I, compared to protein expression of controls. FIG. 1C: protein expression of test LSCs contacted with test composition II, compared to protein expression of controls.

FIG. 2A: Protein expression of control LSCs not exposed to the chemical composition. FIG. 2B: Protein expression of LSCs exposed to test composition I. FIG. 2C: Protein expression of LSCs exposed to test composition II. Bold lines indicate proteins expressed in different amounts between LSCs exposed to each of the two test chemical compositions.

FIG. 3A: Protein expression of control LSCs not exposed to the chemical composition. FIG. 3B: Protein expression of LSCs exposed to test composition I. FIG. 3C: Protein expression of LSCs exposed to test composition II. Bold lines indicate proteins expressed in different amounts between LSCs exposed to each of the two test chemical compositions.

FIG. 4A: Protein expression of control LSCs not exposed to the chemical composition. FIG. 4B: Protein expression of LSCs exposed to test composition I. FIG. 4C: Protein expression of LSCs exposed to test composition II. Bold lines indicate proteins expressed in different amounts between LSCs exposed to each of the two test chemical compositions.

MODE(S) FOR CARRYING OUT THE INVENTION

A. Definitions

Figure 1:
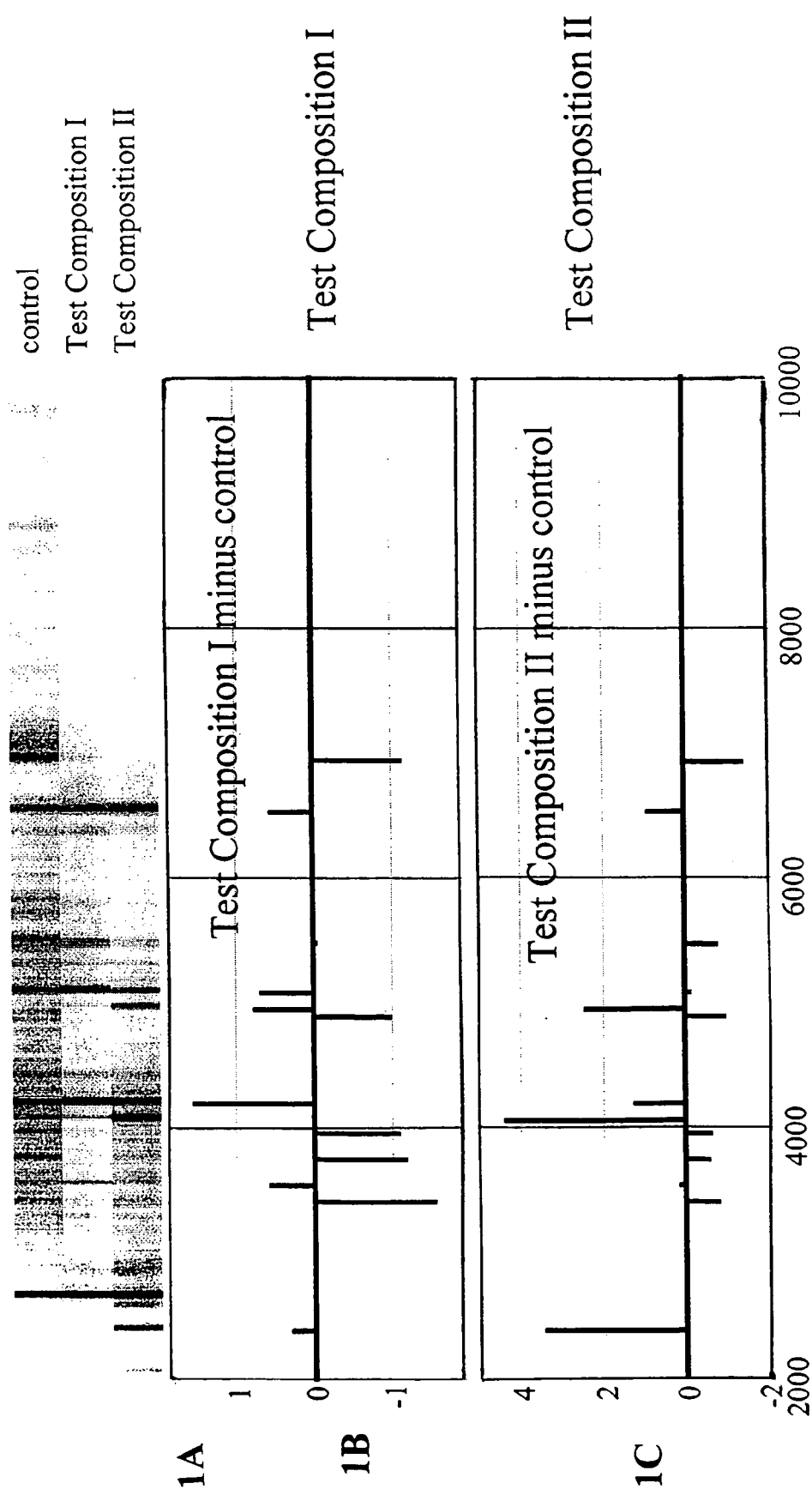
FIG. 1 illustratively depicts differences in expression of nuclear proteins between LSCs exposed to one of two chemical compositions, and control LSCs.

"Toxicity," as used herein, means any adverse effect of a chemical on a living organism or portion thereof. The toxicity can be to individual cells, to a tissue, to an organ, or to an organ system. A measurement of toxicity is therefore integral to determining the potential effects of the chemical on human or animal health, including the significance of chemical exposures in the environment. Every chemical, and every drug, has an adverse effect at some concentration; accordingly, the question is in part whether a drug or chemical poses a sufficiently low risk to be marketed for a stated purpose, or, with respect to an environmental contaminant, whether the risk posed by its presence in the environment requires special precautions to prevent its release, or quarantining or remediation once it is released. See, e.g., Klaassen, et al., eds., *Casarett and Doull's Toxicology: The Basic Science of Poisons*, McGraw-Hill (New York, N.Y., 5$^{th}$ Ed. 1996). As used herein, a chemical composition with "predetermined toxicities" means that the type of toxicities and/or certain pharmacodynamic properties of the chemical composition have been determined. For example, a chemical composition may be known to induce liver toxicity. Furthermore, the severity of liver toxicity caused by the chemical may be quantitatively measured by the amount or concentration of the chemical in contact with the liver tissues.

"Alteration in gene or protein expression" according to the present invention means a change in the expression level of one or more genes or proteins compared to the gene or protein expression level of LSC which has been exposed only to normal tissue culture medium and normal culturing conditions. Depending on the context, the phrase can mean an alteration in the expression of a single protein or gene, as when LSCs exposed to a chemical agent expresses a protein not expressed by control LSCs, or it can mean the overall pattern of gene or protein expression of LSCs. The phrase can include gene or protein expression in LSCs at one or more time points and/or stages along the pathway of their differentiation, growth, and/or development into fully-differentiated liver cells. The phrase does not include gene or protein expression in fully-differentiated liver cells.

"LSC type" or "type of LSC" as used herein refer to LSCs isolated from a particular source (as defined by, for example, species, tissue, age of source) and/or according to a particular LSC isolation method.

"Chemical composition," "chemical," "composition," and "agent," as used herein, are generally synonymous and refer to a compound of interest. The chemical can be, for example, one being considered as a potential therapeutic, an agricultural chemical, an environmental contaminant, or an unknown substance found at a crime scene, at a waste disposal site, or dumped at the side of a road.

As used herein, "molecular profile" or "profile" of a chemical composition refers to a pattern of alterations in gene or protein expression, or both, in LSCs contacted by the chemical composition compared to similar LSCs in contact only with culture medium.

As used herein, "efficacy profile" of a chemical composition refers to the existence and/or extent of an expected, characteristic and/or desired effect(s) of the chemical composition in a cell, tissue, organ, and/or organism. For example, the efficacy profile of a drug known or expected to induce bone development might include an effect such as up-regulation of a gene(s) and/or protein(s) associated with bone development.

As used herein, "database" refers to an ordered system for recording information correlating information about the toxicity, the biological effects, or both, of a chemical agent to the alterations in the pattern of gene or protein expression, or both, in LSCs contacted by a chemical composition compared to like LSCs in contact only with culture medium.

A "library," as used herein, refers to a compilation of molecular profiles of at least two chemical compositions, permitting a comparison of the alterations in gene or protein expression, or both, in LSCs contacted by a chemical composition to the profiles of such expression(s) caused by other chemical compositions.

"Array" means an ordered placement or arrangement. Most commonly, it is used herein to refer to an ordered placement of oligonucleotides (including cDNAs and genomic DNA) or of ligands placed on a chip or other surface used to capture complementary oligonucleotides (including cDNAs and genomic DNA) or substrates for the ligand. For example, since the oligonucleotide or ligand at each position in the arrangement is known, the sequence (of a nucleic acid) or a physical property (of a protein) can be determined by the position at which the nucleic acid or substrate binds to the array.

"Operably linked" means that two or more elements are connected in a way that permits an event occurring in one element (such as a reading by an optical reader) to be transmitted to and acted upon by a second element (such as a calculation by a computer concerning data from an optical reader).

B. General Description

The invention provides methods of assessing toxicity of chemical compositions on a genome-wide basis, in an in vitro system that closely models the complex biological and cellular interactions in vivo. In one aspect, the invention is especially useful in drug development, both because of its ability to validate targets and because of its ability to rapidly identify and to quantify all the expressed genes associated with responses to a potential therapeutic agent.

The invention achieves these goals by exploiting the properties of pluripotent liver stem cells (LSCs). LSCs are the formative pluripotential progenitor cells that are capable of differentiating into multiple epithelial cell types of the liver and/or other tissues/organs, such as the pancreas and intestine. Generally, these are progenitor cells that are capable of developing into either hepatocytes or bile duct cells. However, it is thought that that they are also capable of differentiating into other cell types. LSCs have been found and isolated as hepatoblasts (a preferred form of LSC for the purpose of this invention), generally at the embryonic development stage, in the hepatic diverticulum of the foregut. They have also been isolated from adult liver as cells that have stem cell or stem cell-like characteristics. For the purpose of this invention, oval cells found in adult liver are also LSCs. Because of its pluripotency in differentiating into multiple tissue types, an isolated population of LSCs provides a much closer model to the complexity of in vivo systems than do traditional single cell or yeast assays, while still avoiding the cost and difficulties associated with the use of mice or larger mammals.

For the purpose of the present invention, LSCs possess many advantages over other types of stem cells such as embryonic stem cells (ES). LSCs are relatively easy to isolate and purify from a number of sources. They are also relatively amenable to expansion in culture and to be subject to modified conditions such as drug treatments. Obtaining ES cells, on the other hand, can be very complicated and tend to be labor intensive. In the case of ES cells, use of human or animal embryos may also be subject to ethical and regulatory scrutiny. LSCs also offer a significant advantage over other stem cells in that they are the progenitor cells for the hepatocytes and bile duct cells, which are the predominant cells in liver, which is the organ most susceptible to toxicity due to drugs and other substances (see, for e.g., Table 1). Therefore, toxicity assays that focus on the cellular components and development of the liver would be expected to offer a more direct assessment of the potential toxicity of a significant number of test compounds. Furthermore, since LSCs can be isolated from live individuals, such as through a needle or small wedge biopsy of adult liver, the present invention provides means to enable the development of toxicity profiles for individual patients or patient populations that have unique drug sensitivities, an area that would be almost impossible to achieve if using ES cells for toxicity assay. Recent technology developments allow the isolation of these cells from cadavers in some cases up to 24 hours after death.

The LSCs used in the invention comprise a cell population, the majority of which being pluripotent cells capable of developing into different cellular lineages when cultured under appropriate conditions. It is preferred that the LSC population comprises at least 51% pluripotent cells. More preferably, the LSC population comprises at least 75% pluripotent cells. And still more preferably, the LSC population comprises at least 95% pluripotent cells.

In its simplest form, the method of creating a molecular profile according to the present invention involves contacting LSCs with a chemical composition of interest, and then determining the alterations in gene expression, protein expression, or both, in LSCs exposed to the chemical composition (the "test LSCs") compared to LSCs which are not exposed to the agent (the "control LSCs").

Furthermore, a library can be generated by compiling molecular profiles for two or more different chemical compositions, such as those having similar toxicities. The molecular profiles of these compositions can be compared with each other, either qualitatively or quantitatively, in order to discern common alterations in their gene or protein expression patterns. For example, while the overall gene or protein expression pattern for each chemical composition may be unique, the changes in expression level of certain specific genes or proteins may be similar among compositions having similar toxicities—some genes/proteins may be similarly up-regulated and therefore expressed in higher amount compared to controls; while other genes/proteins may be similarly down-regulated and therefore expressed in smaller amount compared to controls. These common molecular features of the chemical compositions can then be correlated to their toxicities and serve as surrogate markers for assessing the toxicities of a new or previously untested chemical composition, such as a drug lead in drug screening assays.

Thousands of compounds have undergone preclinical and clinical studies. Preclinical studies include, among other things, toxicity studies in at least two mammalian species, one of which is usually a murine species, typically mice or rats, and clinical trials always include information on any apparent toxicity. A considerable amount of information is available about the toxicity of various of these compounds. Based on the toxicity information available, these compounds can be classified into particular categories of toxicities. For example, a number of chemical compositions are listed in Table 1 according to tissues or organs in which they exert toxicities.

TABLE 1

| | TOXICITIES | | | | | |
|---|---|---|---|---|---|---|
| | EV | IVER | V | NS | LOOD | INDICATION | TRADE NAMES |
| DRUGS | | | | | | |
| thalidomide | | | | | | |
| methotrexate | | | | | | antineoplastics | |
| retinoic acid | | | | | | acne | |
| valproic acid | | | | | | seizures | Depakene |
| acetominophen | | | | | | analgesic | |
| isoniazid | | | | | | antibiotic | |
| diclofenac (NSAIDS) | | | | | | anti-inflammatory | Voltarem |
| bromofenac (NSAIDS) | | | | | | anti-inflammatory | Duract |
| troglitazone | | | | | | diabetes | Rezulin ™ |
| rosiglitazone | | tc | | | | diabetes | Avandia ™ |
| trovaflozacin | | | | | | antibiotic | Trovan ™ |
| ciprofloxacin | | tc | | | | antibiotic | Cipro ™ |
| erythromycin estolate | | | | | | antibiotic | |
| pravastatin | | | | | | lipid lowering | Pravachol ™ |
| atorvastin | | | | | | lipid lowering | Lipitor ™ |
| clofibrate | | tc | | | | lipid lowering | Atromid |
| clozapine | | | | | | antipsychotic | Clozaril |
| chloroamphenicol | | | | | | antibiotic | Chloromycetin |
| doxorabicin | | | | | | antineoplastics | |
| dannorubicin | | | | | | antineoplastics | |
| cyclosophosphamide | | | | | | antineoplastics | |

TABLE 1-continued

| COMPOUNDS | EV | IVER | V | NS | LOOD | INDICATION | TRADE NAMES |
|---|---|---|---|---|---|---|---|
| carbon tetrachloride | | | | | | | |
| cadmium | | | | | | | |
| phallodidin | | | | | | | |
| ethanol | | | | | | | |
| di-methyl formide | | | | | | | |
| dichlorethylene | | | | | | | |
| lead | | | | | | | |
| benzo(a)pyrene | | | | | | | |
| allylamine | | | | | | | |
| methylmercury | | | | | | | |
| trimethyltin | | | | | | | |
| carbon disulfide | | | | | | | |
| acrylamide | | | | | | | |
| hexachloraphene | | | | | | | |
| DMSO | | not well studied | | | | | |

"ntc" = non-toxic, limited toxicity, control
"Dev" = developmental
"CV" = cardiovascular
"CNS" = central nervous system In one embodiment of the invention, compositions known for having liver toxicities are used for a systematic analysis of their molecular profiles in LSCs. In another embodiment, compositions causing toxicities to the cardiovascular system are evaluated for their molecular profiles in LSCs. In yet another embodiment of the invention, compositions causing toxicities to the neuronal system are evaluated for their molecular profiles in LSCs. Alternatively, known or potential drugs for treating a disease of choice can be used together in a systematic analysis of their toxicities. In this regard, for example, anti-cancer drugs and drug candidates can be screened for their tissue and organ toxicities.

According to one aspect of the invention, molecular profiles of chemical compositions can be correlated to toxicities these agents demonstrated in non-human animals, in humans, or in both. By then comparing the expression pattern of LSCs exposed to a new or previously untested agent to a library of such profiles of expression induced by agents of known toxicity, predictions can be made as to the likely type of toxicity of the new agent. Furthermore, the toxicity of the new agent, if any, can be ranked among the known toxic compositions, providing information for prioritization in drug development.

In addition to its utility in drug development, the invention also has uses in other arenas in which the toxicity of chemical compositions is of concern. Thus, the invention can be utilized to assess the toxicity of agricultural chemicals, such as pesticides and fertilizers. It can further be used with cosmetics. For example, it can be used to screen candidate cosmetics for toxicity prior to moving the compounds into animal studies, thereby potentially reducing the number of animals which need to be subjected to procedures such as the Draize eye irritancy test. Similarly, the methods of the invention can be applied to agents intended for use as "cosmeceuticals," wherein agents which are primarily cosmetic are also asserted to have some quasi-therapeutic property. Further, the invention can be used to assess the relative toxicity of environmental contaminants, including waste products, petrochemical residues, combustion products, and products of industrial processes. Examples of such contaminants include dioxins, PCBs, and hydrocarbons.

In general, it is preferred that the method used to detect the levels of protein or gene expression provides at least a relative measure of the amount of protein or gene expression. More preferably, the method provides a quantitative measure of protein or gene expression to facilitate the comparison of the protein or gene expression of the LSCs exposed to the test chemical composition to that of LSCs. exposed to chemical compositions of known toxicity.

C. Preparing LSCs

Methods for preparing LSCs of human or other mammalian species are known in the art. For example, Reid et al., U.S. Pat. Nos. 5,576,207 and 5,789,246, describe methods for isolation and expansion of immature cells whose progeny may differentiate into various liver cells. These cells can be isolated from various tissues, including liver, pancreas, gut, lung and bone marrow. The immature (precursor) cells can be dissociated from the tissue source by standard procedures such as enzymatic and mechanical dissociation. The dissociated cell population can further be enriched for precursor cells by standard methods, such as using antibodies that recognize an epitope of the precursor cells (such epitopes are known in the art, and examples are provided below). Expansion of the precursor cells is achieved by culturing the cells in the presence of an extracellular matrix, liver stromal cells and growth factors. Other conditions suitable for isolation and expansion of these cells are also disclosed. These precursor cells may differentiate into hepatocytes, bile duct cells, liver endothelial cells, and Ito cells.

Methods of isolating hepatoblasts are also known. For example, Reid et al., U.S. Pat. No. 6,069,005, describe an isolation method using panning techniques and fluorescence activated cell sorting. These hepatic progenitor cells are isolated by dissociating liver cells, followed by panning and sorting (by fluorescence activated cell sorting) utilizing antibodies to reduce the amount of contaminating cell types.

Another method for isolating, characterizing and culturing liver progenitor cells is described in Naughton et al., U.S. Pat. No. 5,559,022. Liver progenitor cells are isolated by density gradient centrifugation, and distinguished from other liver parenchymal cells by their morphology, staining characteristics, high proliferative activity and ability to differentiate in vitro.

Another method for obtaining liver stem cells is described in Faris, PCT Publication WO00/03001. Faris describes methods of isolating primary liver stem cells from fetal, pediatric or adult liver tissue that is based on the propensity of liver stem cells to participate in cell clusters with hepatocytes, with further enrichment achieved by immunosubtraction, selective enzymatic digestion and antibody affinity selection.

Isolation of bile duct progenitor cells which are capable of giving rise to various differentiated cells, including cells of the hepatic lineage, is described in Pang et al., U.S. Pat. No. 5,861,313. A population of cells having a microarchitecture of a mammalian bile duct, such as a bile duct explant, is cultured, and contacted with agents that cause proliferation of progenitor cells in the cultured population. Subsequently, the progenitor cells are isolated, such as by direct mechanical separation from the rest of the explant or by dissolution of all or a portion of the explant. Various conditions suitable for isolation and culturing of the progenitor cells are provided in the reference.

Isolation of conditionally transformed liver progenitor cells with phenotypic similarities to hepatoblasts has also been described. Fiorino et al., *In Vitro Cell. Dev. Biol.— Animal* (1998), 34:247-258, describe the isolation of cells capable of being induced to express various differentiation markers of liver cells.

The lineage-specific differentiation of LSCs can be induced by various bioactive factors and/or conditions that are well known in the art. These are described in, for example, Brill et al., Extracellular matrix regulation of growth and gene expression in liver cell lineages and hepatomas In Liver Biology and Pathobiology (1994), pp. 869-897 (Raven Press, N.Y.); Reid and Luntz, Ex vivo maintenance of differentiated mammalian cells In Basic Cell Culture Protocols (1997), 75:31-57 (Humana Press, Totowa, N.J.); Reid and Luntz (1997), *Methods in Molecular Biology* (1997), 75:31-57; see, generally, Reid, Stem cell/lineage biology and lineage-dependent extracellular matrix chemistry: keys to tissue engineering of quiescent tissues such as liver In Textbook of Tissue Engineering (1997), (R. G. Landes/Academic Press, Austrin, Tex.); Brill et al., *Differentiation* (1995), 59:95-102; Brill et al., *Digestive Diseases & Sciences* (1999), 44:364-371; and Faris, PCT Publication WO00/03001. For example, differentiation of liver progenitor cells can be achieved by removal of conditions known to maintain the cells in undifferentiated form or by administering one of several known growth factors, such as HGF, FGF and IGF-II. Differentiation of liver stem cells can also be induced by contact with liver tissue, i.e., other hepatocytes or cell matrix components known in the art. Presence of dexamethasone in culture medium has been shown to induce differentiation of embryonic mouse liver cells along both the hepatocyte and bile duct lineages. Supplementation of culture medium with serum, insulin, dexamethasone and dimethyl sulfoxide induces cells isolated from E12 rat liver to express hepatocyte markers, whereas exposure of these cells to sodium butyrate causes expression of bile duct cell markers. See, generally, Grisham and Thorgeirsson, Liver stem cells In Stem Cells pp. 233-282 (Academic Press, London) (1997); Shiojiri and Mizuno, *Anat. Embryol.* (1993), 187:221-229; Gall and Bhathal, *J. Exp. Pathol.* (1990), 71:41-50; and Germain et al., *Cancer Res.* (1988), 48:4909:4918.

LSCs obtained for use in the present invention can be identified by their distinct properties as known in the art and described in references cited herein. For example, liver stem cells tend to be smaller than their more differentiated descendants, have a high nuclear to cytoplasmic ratio, undifferentiated and pale nuclei, and a few intercellular adhesions. Reid et al., U.S. Pat. No. 6,069,005. Naughton et al. describe the hepatic progenitor cells isolated by their method as having a low nuclear to cytoplasmic ratio, staining with specific characteristics when contacted with a combination of acidic and basic stains, and having higher proliferation rates in culture than do mature liver cells. Naughton et al., U.S. Pat. No. 5,559,022.

Alternatively, the LSCs used in the present invention can be identified by the detection of specific markers such as through the use of antibodies specific to a population of LSCs at a defined stage. For example, Grisham and Thorgeirsson, supra, describe a substantial list of antibody markers commonly used to assess differentiation and to trace lineage of liver epithelial cells, including OC.2 and OC.3, which are markers expressed in hepatoblasts but not hepatocytes. Also, antibodies to cytokeratins could be useful in evaluating liver epithelial cell lineage and differentiation. For example, Moll et al., *Cell* (1982), 31:11-24; Osborn and Weber, *Cell* (1982), 31:303-306; Marceau, *Lab. Invest.* (1990), 63:4-20; Shiojiri et al., *Cancer Res.* (1991), 51:2611-2620; and Blouin et al., *Differentiation* (1992), 52:45-54, have reported that all types of epithelial cells express combinations of between two and ten cytokeratins (CK), and that the particular combination of CKs expressed by the cells, such as the combination of CKs that are the equivalent to human CKs 8, 18, 7, and 19 (and rarely CK 14), indicate differentiated forms of liver epithelial cells.

If necessary, LSCs obtained and cultured for use in the present invention may be isolated from the culture based on their physical or chemical properties (such as size, mass, density, specific antigen or gene expression), using methods known in the art (such as flow cytometry, cell sorting, filtration or centrifugation).

The LSCs used to test the chemical composition can be of any vertebrate species. The choice of the particular species from which the LSCs are derived will typically reflect a balance of several factors. First, depending on the purpose of the study, one or more species may be of particular interest. For example, human LSCs will be of particular interest for use with compositions being tested as potential human therapeutics, while equine, feline, bovine, porcine, caprine, canine, or sheep LSCs may be of more interest for a potential veterinary therapeutic.

Second, even with respect to testing of human therapeutics, cost and handling considerations may dictate that some or all testing be performed with non-human, and even non-primate LSCs. For some testing, it may be desirable to use LSCs from mice, rats, guinea pigs, rabbits, and other readily available, and less expensive, laboratory animals.

Third, it will often be of value to select a species as to which considerable information is available on the toxicity of chemical compositions, so that observed changes in gene and protein expression can be correlated to various types of toxicity. For this reason, mice and rats are preferred embodiments. Most pre-clinical testing is performed on at least one murine species, and there therefore exists a large body of information on the toxicity of various compounds on various tissues of mice and on rats. Using LSCs derived from mice or rats permits the correlation of the alterations in gene or protein expression in the LSCs with the toxicities exhibited by these agents in those species. LSCs of other species commonly used in preclinical testing, such as guinea pigs, rabbits, pigs, and dogs, are also preferred for the same reason. Typically, LSCs of these species will be used for "first pass" screening, or where detailed information on toxicity in humans is not needed, or where a result in a murine or other one of these laboratory species has been correlated to a known toxicity or other effect in humans.

Fourth, although primates are not as widely used in preclinical testing and are often more expensive to purchase and to maintain than other laboratory animals, their biochemistry and developmental biology is considerably closer to that of humans than those of the more common laboratory animals. LSCs derived from primates is therefore preferred for toxicity testing where the study is sufficiently important to justify the additional cost and handling considerations. Most preferred are human LSCs, since conclusions about the toxicity of agents in these LSCs can be considered the most directly relevant to the effect of a chemical composition on humans. It is anticipated that studies in primate or human LSCs will be performed to confirm results of toxicity studies in LSCs of other species.

Fifth, with respect to human therapeutics, regulatory agencies generally require animal data before human trials can begin; it will generally be desirable to use LSCs of species which will be used in the preclinical animal studies. The results of toxicity testing in the LSCs can then guide the researcher on the degree and type of toxicity to anticipate during the animal trials. Certain animal species are known in the art to be better models of human toxicity of different types than are others, and species also differ in their ability to metabolize drugs. See, e.g., Williams, *Environ Health Perspect.* (1978), 22:133-138; Duncan, *Adv. Sci.* (1967), 23:537-541. Thus, the particular species preferred for use in a particular preclinical toxicity study may vary according to the intended use of the drug candidate. For example, a species which provides a suitable model for a drug intended to affect the reproductive system may not be as suitable a model for a drug intended to affect the nervous system. Criteria for selecting appropriate species for preclinical testing are well known in the art.

While LSCs from different species can be used in the methods of the invention, in general, mammalian cells are preferred. In the discussions below, it is assumed that in any given comparison of control and test LSCs, the LSCs used as controls and those used to test the effects of the chemical compositions are derived from the same species.

D. Contacting LSCs with Chemical Compositions
1. General

Once a LSC culture has been initiated, it can be contacted with a chemical composition. Conveniently, the chemical composition is in an aqueous solution and is introduced to the culture medium. The introduction can be by any convenient means, but will usually be by means of a pipette, a micropipettor, or a syringe. In some applications, such as high throughput screening, the chemical compositions will be introduced by automated means, such as automated pipetting systems, which may be on robotic arms. Chemical compositions can also be introduced into the medium as in powder or solid forms, with or without pharmaceutical excipients, binders, and other materials commonly used in pharmaceutical compositions, or with other carriers which might be employed in the intended use. For example, chemical compositions intended for use as agricultural chemicals or as petrochemical agents can be introduced into the medium: by themselves to test the toxicity of those chemicals or agents, or introduced in combination with other materials with which they might be used or which might be found in the environment, to determine if the combination of the chemicals or agents has a synergistic effect. Typically, the cultures will be shaken at least briefly after introduction of a chemical composition to ensure the composition is dispersed throughout the medium.

2. Timing of Contacting

The time at which a chemical composition is added to the culture is within the discretion of the practitioner and will vary with the particular study objective. Conveniently, the chemical composition will be added as soon as the LSCs are cultured, permitting the determination of the alteration in protein or gene expression on the development of all the tissues of the LSCs. It may be of interest, however, to focus the study on the effect of the composition on a particular liver cell type. As previously noted, individual differentiated cells, such as hepatocytes and bile duct cells, are known to develop in the presence of specific inducing factors and/or conditions, and can be identified by specific cell markers. Such factors, conditions and markers are known in the art, and examples are provided herein and in the references cited. Addition of the chemical composition can therefore be staged to occur at various time points and/or stages in the differentiation, growth and/or development of the LSCs. In one embodiment, the chemical composition is contacted with LSCs maintained in undifferentiated form. In another embodiment, addition of the chemical composition is staged to occur at the time the cell type/tissue of interest commences developing. In yet another embodiment, the addition of the chemical composition is staged to occur at a chosen time point after commencement of that development, in order to observe the effect on altering gene or protein expression in the cell type/tissue of interest.

3. Dosing of the Chemical Composition

Different amounts of a chemical composition will be used to contact LSCs depending on the amount of information known about the cytotoxicity of that composition, the purposes of the study, the time available, and the resources of the practitioner. A chemical composition can be administered at just one concentration, particularly where other studies or past work or field experience with the compound have indicated that a particular concentration is the one which is most commonly found in the body. More commonly, the chemical composition will be added in different concentrations to cultures of LSCs run in parallel, so that the effects of the concentration differences on gene or protein expression and, hence, the differences in toxicity of the composition at different concentrations, can be assessed. Typically, for example, the chemical composition will be added at a normal or medium concentration, and bracketed by twofold or fivefold increases and decreases in concentration, depending on the degree of precision desired.

Where the composition is one of unknown cytotoxicity, a preliminary study is conveniently first performed to determine the concentration ranges at which the composition will be tested. A variety of procedures for determining concentration dosages are known in the art. One common procedure, for example, is to determine the dosage at which the agent is directly cytotoxic. The practitioner then reduces the dose by one half and performs a dosing study, typically by administering the agent of interest at fivefold or twofold dilutions of concentration to parallel cultures of cells of the type of interest. For environmental contaminants, the composition will usually also be tested at the concentration at which it is found in the environment. For agricultural chemicals, such as pesticides which leave residues on foodstuffs, the agent will usually be tested at the concentration at which the residue is found, although it will likely be tested at other concentrations as well.

In one embodiment, the toxicity profile(s) (e.g., molecular profile) of a chemical composition in LSCs is correlated with the concentration(s) at which the chemical composition is contacted with the LSCs. Such a correlation can provide useful indication of the concentration(s) of the chemical composition that causes acceptable or unacceptable extents of cytotoxicity. In another embodiment, the efficacy profile(s) of a chemical composition in LSCs is correlated with the concentration(s) at which the chemical composition is contacted with the LSCs. Such a correlation can provide useful indication of the concentration(s) of the chemical composition sufficient to cause an acceptable and/or desirable degree of efficacy of the composition. In yet another embodiment, the toxicity profile-concentration correlation and the efficacy profile-concentration correlation are used in an index that provides a measurement of the desirability and/or usefulness of the chemical composition. For example, a highly desirable chemical composition would be one that has an index that is a function of high concentration for causing an unacceptable level of LSC toxicity and low concentration for obtaining a desirable and/or useful level of efficacy.

E. Detecting Alterations in Levels of Gene or Protein Expression

1. Detecting Protein Expression Alterations

Protein expression can be detected by a number of methods known in the art. For example, the proteins in a sample can be separated by sodium dodecyl sulphate-polyacrylamide gel electrophoresis ("SDS-PAGE") and visualized with a stain such as Coomassie blue or a silver stain. Radioactive labels can be detected by placing a sheet of X-ray film over the gel. Proteins can also be separated on the basis of their isoelectric point via isoelectric focusing, and visualized by staining. Further, SDS-PAGE can be performed in combination with isoelectric focusing (usually performed in perpendicular directions) to provide two-dimensional separation of the proteins in a sample. Proteins can further be separated by such techniques as high pressure liquid chromatography, HPLC, thin layer chromatography, affinity chromatography, gel-filtration chromatography, ion exchange chromatography, surface enhanced laser desorption/ionization ("SELDI"), matrix-assisted laser desorption/ionization ("MALDI"), and, if the sedimentation rates are sufficiently different, density gradient centrifugation. Detecting alterations in levels of protein expression using these techniques can be accomplished, for example, by running in parallel samples from LSCs contacted with a chemical composition whose effect is of interest ("test samples") and samples from LSCs cultured under identical conditions except for the presence of the chemical composition of interest ("control samples"), and noting any differences in the proteins detected and the amount of the proteins detected.

Immunodetection provides a group of useful techniques for detecting alterations in protein expression. In these techniques, antibodies are typically raised against the protein by injecting the protein into mice or rabbits following standard protocols, such as those taught in Harlow and Lane, *Antibodies, A Laboratory Manual* (Cold Spring Harbor Laboratory, Cold Spring Harbor, N.Y., 1988). The antibodies so raised can then be used to detect the presence of and quantitate the protein in a variety of immunological assays known in the art, such as ELISAs, fluorescent immunoassays, Western and dot blots, immunoprecipitations, and focal immunoassays. Alterations in protein expression can be determined by running parallel tests on test and control samples and noting any differences in results between the samples. Results of ELISAs, for example, can be directly related to the amount of protein present.

Tagging provides another way to detect and determine changes in protein expression. For example, the gene encoding the protein can be engineered to produce a hybrid protein containing a detectable tag, so that the protein can be specifically detected by detection of the tag. Systems are available which permit the direct imaging and quantitation of radioactive labels in, for example, gels on which the proteins have been separated. Differences in expression can be determined by observing differences in the amount of the tag present in test and control samples.

Proteins can also be analyzed by standard protein chemistry techniques. For example, proteins can be analyzed by performing proteolytic digests with trypsin, Staphylococcus B protease, chymotrypsin, or other proteolytic enzymes. Differences in expression can be determined by comparing relative amounts of the digested products.

One particularly preferred method for determining differences in protein expression is mass spectroscopy, or "MS," which provides the broadest profile of the broadest number of proteins for the least effort. Moreover, MS permits not only accurate detection of proteins present in a sample, but also quantitation. The procedure can be used either by itself, or in combination with one or more of the preceding methods based on selective physical properties to partition the proteins present in a sample. Partitioning reduces the number of proteins of different physical properties in the sample and results in a better MS analysis by permitting a comparison of proteins of similar size, electrostatic charge, affinity for metal ions, or the like. Thus, for example, the proteins in a sample can be subjected to SDS-PAGE and isoelectric focusing, and a resulting spot of interest on the gel can then be subjected to MS. In Example 2, below, an initial partitioning performed using a sizing column and a second partitioning performed using SELDI are illustrated. It should be noted that, in the protocol described in Example 2, analysis of proteins with molecular weights smaller than 30 kD is exemplified. Alternatively, of course, the higher weight proteins could be analyzed in the methods of the invention, and the proteins do not need to be fractionated if the practitioner is prepared to analyze all the proteins in a sample or, for example, if a preliminary analysis shows that the total number of different proteins in a sample is small enough to be analyzed without partitioning.

Computers attached to the mass spectrometer can also be used to analyze the samples to facilitate determination of whether a change in protein expression may be indicative of a particular toxicity. For example, the readout from the MS can be used in a "subtractive calculation" in which the protein expression in control LSCs is quantitated and then subtracted from the quantitated protein expression of LSCs contacted with a chemical composition, with only the proteins expressed in greater or lesser quantities than those expressed by the control LSCs being shown. This method immediately focuses attention on differences in protein expression between a control and a test population. Examples of such comparisons are shown in FIGS. 1B and 1C and discussed in detail below.

2. Detecting Gene Expression Alterations

A number of methods are known in the art for detecting and comparing levels of gene expression.

One standard method for such comparisons is the Northern blot. In this technique, RNA is extracted from the sample and loaded onto any of a variety of gels suitable for RNA analysis, which are then run to separate the RNA by size, according to standard methods (see, e.g., Sambrook, J., et al., Molecular Cloning, A Laboratory Manual. Cold Spring Harbor Laboratory Press, Cold Spring Harbor, N.Y. (2nd ed. 1989)). The gels are then blotted (as described in Sambrook, supra), and hybridized to probes for RNAs of interest. The probes can be radioactive or non-radioactive, depending on the practitioner's preference for detection systems. For example, hybridization with the probe can be observed and analyzed by chemiluminescent detection of the bound probes using the "Genius System," (Boehringer Mannheim Corporation, Indianapolis, Ind.), following the manufacturer's directions. Equal loading of the RNA in the lanes can be judged, for example, by ethidium bromide staining of the ribosomal RNA bands. Alternatively, the probes can be radiolabeled and detected autoradiographically using photographic film.

The RNA can also be amplified by any of a variety of methods and then detected. For example, Marshall, U.S. Pat. No. 5,686,272, discloses the amplification of RNA sequences using ligase chain reaction, or "LCR." LCR has been extensively described by Landegren et al., Science (1988), 241: 1077-1080; Wu et al., Genomics (1989), 4:560-569; Barany, in PCR Methods and Applications, 1:5-16 (1991); and Barany, Proc. Natl. Acad. Sci. USA (1991), 88:189-193. Or, the RNA can be reverse transcribed into DNA and then amplified by LCR, polymerase chain reaction ("PCR"), or other methods. An exemplar protocol for conducting reverse transcription of RNA is taught in U.S. Pat. No. 5,705,365. Selection of appropriate primers and PCR protocols are taught, for example, in Innis, M., et al., eds., PCR Protocols 1990 (Academic Press, San Diego Calif.) (hereafter "Innis et al."). Differential expression of messenger RNA can also be compared by reverse transcribing mRNA into cDNA, which is then cleaved by restriction enzymes and electrophoretically separated to permit comparison of the cDNA fragments, as taught in Belyavsky, U.S. Pat. No. 5,814,445.

Typically, primers are labeled at the 5' terminus with biotin or with any of a number of fluorescent dyes. Probes are usually labeled with an enzyme, such as horseradish peroxidase (HRP) and alkaline phosphatase (see, Levenson and Chang, Nonisotopically Labeled Probes and Primers in Innis, et al., supra), but can also be labeled with, for example, biotin-psoralen. Detailed exemplar protocols for labeling primers and for synthesizing enzyme-labeled probes are taught by Levenson and Chang, supra. Or, the probes can also be labeled with radioactive isotopes. An exemplar protocol for synthesizing radioactively labeled DNA and RNA probes is set forth in Sambrook et al., supra. Usually, $^{32}p$ is used for labeling DNA and RNA probes. A number of methods for detection of PCR products are known. See, e.g., Innis, supra, which sets forth a detailed protocol for detecting PCR products using non-isotopically labeled probes. Generally, there is a step permitting hybridization of the probe and the PCR product, following which there are one or more development steps to permit detection.

For example, if a biotinylated psoralen probe is used, the hybridized probe is incubated with streptavidin HRP conjugate and then incubated with a chromogen, such as tetramethylbenzidine (TMB). Alternatively, if the practitioner has chosen to employ a radioactively labeled probe, PCR products to which the probe has hybridized can be detected by autoradiography. As another example, biotinylated dUTP (Bethesda Research Laboratories, Md.) can be used during amplification. The labeled PCR products can then be run on an agarose gel, Southern transferred to a nylon filter, and detected by, for example, a streptavidin/alkaline phosphatase detection system. A protocol for detecting incorporated biotinylated dUTP is set forth, e.g., in Lo et al., Incorporation of Biotinylated dUTP, in Innis et al., supra. Finally, the PCR products can be run on agarose gels and nucleic acids detected by a dye, such as ethidium bromide, which specifically recognizes nucleic acids.

Sutcliffe, U.S. Pat. No. 5,807,680, teaches a method for the simultaneous identification of differentially expressed mRNAs and measurement of relative concentrations. The technique, which comprises the formation of cDNA using anchor primers followed by PCR, allows the visualization of nearly every mRNA expressed by a tissue as a distinct band on a gel whose intensity corresponds roughly to the concentration of the mRNA.

Another group of techniques employs analysis of relative transcript expression levels. Four such approaches have recently been developed to permit comprehensive, high throughput analysis. First, cDNA can be reverse transcribed from the RNAs in the samples (as described in the references above), and subjected to single pass sequencing of the 5' and 3' ends to define expressed sequence tags for the genes expressed in the test and control samples. Enumerating the relative representation of the tags from the different samples provides an approximation of the relative representation of the gene transcript within the samples.

Second, a variation on ESTs has been developed, known as serial analysis of gene expression, or "SAGE," which allows the quantitative and simultaneus analysis of a large number of transcripts. The technique employs the isolation of short diagnostic sequence tags and sequencing to reveal patterns of gene expression characteristic of a target function, and has been used to compare expression levels, for example, of thousands of genes in normal and in tumor cells. See, e.g., Velculescu, et al., Science (1995), 270:368-369; Zhang, et al., Science (1997), 276:1268-1272.

Third, approaches have been developed based on differential display. In these approaches, fragments defined by specific sequence delimiters can be used as unique identifiers of genes, when coupled with information about fragment length within the expressed gene. The relative representation of an expressed gene within a cell can then be estimated by the relative representation of the fragment associated with that gene. Examples of some of the several approaches developed to exploit this idea are the restriction enzyme analysis of differentially-expressed sequences ("READS") employed by Gene Logic, Inc., and total gene expression analysis ("TOGA") used by Digital Gene Technologies, Inc. CLONTECH, Inc. (Palo Alto, Calif.), for example, sells the Delta™ Differential Display Kit for identification of differentially expressed genes by PCR.

Fourth, in preferred embodiments, the detection is performed by one of a number of techniques for hybridization analysis. In these approaches, RNA from the sample of interest is usually subjected to reverse transcription to obtain labeled cDNA. The cDNA is then hybridized, typically to oligonucleotides or cDNAs of known sequence arrayed on a chip or other surface in a known order. The location of the oligonucleotide to which the labeled cDNA hybridizes provides sequence information on the cDNA, while the amount of labeled hybridized RNA or cDNA provides an estimate of the relative representation of the RNA or cDNA of interest. Further, the technique permits simultaneous hybridization with two or more different detectable labels. The hybridization results then provide a direct comparison of the relative expression of the samples.

A number of kits are commercially available for hybridization analysis. These kits allow identification of specific RNA or cDNAs on high density formats, including filters, microscope slides, microchips, and technologies relying on mass spectrometry. For example, Affymetrix, Inc. (Santa Clara, Calif.), markets GeneChip™ (probe sequences on a glass surface) arrays containing thousands of different oligonucleotide probes with known sequences, lengths, and locations within the array for high accuracy sequencing of genes of interest. CLONTECH, Inc.'s (Palo Alto, Calif.) Atlas™ cDNA Expression Array (a nylon membrane that is spotted in duplicate with 200- to 600-base-pair cDNA fragments representing 588 genes) permits monitoring of the expression patterns of 588 selected genes. Hyseq, Inc.'s (Sunnyvale, Calif.) Gene Discovery Module permits high throughput screening of RNA without previous sequence information at a resolution of 1 mRNA copy per cell. Incyte Pharmaceuticals, Inc. (Palo Alto, Calif.) offers microarrays containing, for example, ordered oligonucleotides of human cancer and signal transduction genes. Techniques used by other companies in the field are discussed in, e.g., Service. R., Science 282: 396-399 (1998).

3. Labels

Both proteins and genes can be labeled to detect the alteration in levels of expression in the methods of the invention. The term "label" refers to a composition detectable by spectroscopic, photochemical, biochemical, immunochemical, or chemical means. For example, useful nucleic acid and protein labels include $^{32}$P, $^{35}$S, fluorescent dyes, electron-dense reagents, enzymes (e.g., as commonly used in an ELISA), biotin, digoxigenin, or haptens and proteins for which antisera or monoclonal antibodies are available.

A wide variety of labels and conjugation techniques are known and are reported extensively in both the scientific and patent literature, and are generally applicable to the present invention for the labeling of nucleic acids, amplified nucleic acids, and proteins. Suitable labels include radionucleotides, enzymes, substrates, cofactors, inhibitors, fluorescent moieties, chemiluminescent moieties, magnetic particles, and the like. Labeling agents optionally include, e.g., monoclonal antibodies, polyclonal antibodies, proteins, or other polymers such as affinity matrices, carbohydrates or lipids. Detection of labeled nucleic acids or proteins may proceed by any of a number of methods, including immunoblotting, tracking of radioactive or bioluminescent markers, Southern blotting, Northern blotting, or other methods which track a molecule based upon size, charge or affinity. The particular label or detectable moiety used and the particular assay are not critical aspects of the invention.

The detectable moiety can be any material having a detectable physical or chemical property. Such detectable labels have been well developed in the field of gels, columns, and solid substrates, and in general, labels useful in such methods can be applied to the present invention. Thus, a label is any composition detectable by spectroscopic, photochemical, biochemical, immunochemical, electrical, optical or chemical means. Useful labels in the present invention include fluorescent dyes (e.g., fluorescein isothiocyanate, Texas red, rhodamine, and the like), radiolabels (e.g., $^{3}$H, $^{125}$I, $^{35}$S, $^{14}$C, or $^{32}$P), enzymes (e.g., LacZ, CAT, horse radish peroxidase, alkaline phosphatase and others, commonly used as detectable enzymes, either as marker gene products or in an ELISA), nucleic acid intercalators (e.g., ethidium bromide) and colorimetric labels such as colloidal gold or colored glass or plastic (e.g. polystyrene, poly-propylene, latex, etc.) beads, as well as electronic transponders (e.g., U.S. Pat. No. 5,736,332).

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule. Bruchez et al., *Science* (1998), 281: 2013-2016. Similarly, highly fluorescent quantum dots (zinc sulfide-capped cadmium selenide) have been covalently coupled to biomolecules for use in ultrasensitive biological detection. Warren and Nie, *Science* (1998), 281: 2016-2018.

The label is coupled directly or indirectly to the desired nucleic acid or protein according to methods well known in the art. As indicated above, a wide variety of labels may be used, with the choice of label depending on the sensitivity required, ease of conjugation of the compound, stability requirements, available instrumentation, and disposal provisions. Non-radioactive labels are often attached by indirect means. Generally a ligand molecule (e.g., biotin) is covalently bound to a polymer. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled anti-ligands. Alternatively, any haptenic or antigenic compound can be used in combination with an antibody.

Labels can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, fluorescent green protein, and the like. Chemiluminescent compounds include luciferin, and 2,3-dihydrophthalazinediones, e.g., luminol.

Means of detecting labels are well known to those of skill in the art. Thus, for example, where the label is a radioactive label, means for detection include a scintillation counter, proximity counter (microtiter plates with scintillation fluid built in), or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDS) or photomultipliers and the like. Similarly, enzymatic labels may be detected by providing appropriate substrates for the enzyme and detecting the resulting reaction product. Finally, simple colorimetric labels are often detected simply by observing the color associated with the label. Thus, in various dipstick assays, conjugated gold often appears pink, while various conjugated beads appear the color of the bead.

F. Correlating Molecular Profiles with Toxicities

The invention contemplates multiple iterations of compiling a library of molecular profiles by contacting test LSCs with an ever-widening group of chemical compositions having predetermined toxicities. The toxicities and biological effects of many chemical compositions are already known through previous animal or clinical testing. Any such information is carefully noted along with the alterations of gene or protein expression in LSCs. As the data from tests on a number of chemical compositions, or agents, is gathered, it is assembled to form a library. Separate libraries can be maintained for each type of toxicity; preferably, a single database can be maintained recording the results of all the tests conducted and any available toxicity information on the agents to which the LSCs were exposed. Preferably, biological effects are also noted. Past experience has indicated that biological effects often become associated with, or markers for, particular toxicities as the biology of the toxicity becomes better understood.

In one group of embodiments, libraries are compiled comprising molecular profiles of one or more types of LSCs, which may include one or more of those listed in Table 2, contacted with one or more chemical compositions with predetermined toxicities, which may include one or more of those listed in Table 1.

TABLE 2

Examples of types of LSCs

| Species | Source | Isolation method |
| --- | --- | --- |
| Various, including human, rodent, rabbit, bovine | Various, including liver, pancreas, gut, lung, bone marrow | Reid et al., U.S. Pat. No. 5,576,207 and 5,789,246 |
| Rat | Day 14 fetal liver | Reid et al., U.S. Pat. No. 6,069,005 |
| Rat | Day 15 fetal liver | Reid et al., U.S. Pat. No. 6,069,005 |
| Rat | 69 week adult liver | Naughton et al., U.S. Pat. No. 5,559,022 |
| Rat | Adult liver | Faris, PCT Publication WO00/03001 |
| Rat or mouse | Adult or neonatal common bile duct | Pang et al., U.S. Pat. 5,861,313 |

The invention contemplates that each iteration of contacting test LSCs with a chemical composition will generate a pattern of gene or protein expression, or both, characteristic for that chemical composition and/or LSC type. The determination of the alteration in gene or protein expression of a reasonably large number of chemical compounds of similar toxicity is desirable so that patterns of gene or protein expression, or both, associated with that toxicity can be determined. Changes in gene or protein expression patterns in LSCs that are common to classes of drugs that have similar toxicities will serve as surrogate molecular profiles useful for recognizing compounds that are likely to have related biology and toxicities. It is the correlation of these alterations in gene or protein expression and toxicities that gives the invention its predictive power with respect to previously untested compounds.

The correlation of patterns of gene or protein expression with toxicities can be performed by any convenient means. For example, visual comparisons of patterns can be performed to determine patterns associated with different types of toxicities. More conveniently, the correlation can be done by computer, using one of the statistical programs discussed in the following section. Preferably, the correlation is performed by a computer using non-parametric statistical methods or neural network programs, since neural network programs are specifically designed for pattern recognition. Once a correlation of expression markers which are biomarkers for a particular toxicity has been made, a comparison can be made, again conveniently by computer, of known patterns to the pattern of gene or protein expression induced by a new or unknown chemical composition to provide the closest matches of expression. The patterns can then be reviewed to predict the likely toxicity of the new or unknown chemical.

G. Typing and Ranking Toxicities of Test Chemical Compositions

A molecular profile of a test chemical composition can be established by detecting the alterations in gene or protein expression in LSCs contacted by the test chemical composition as described in the previous sections. Once the molecular profile of the test composition is determined, it can be compared to that of a chemical composition with predetermined toxicities or, preferably, to a library of molecular profiles of chemical compositions with predetermined toxicities. The outcome of such comparison provides information for one to predict the likelihood of whether the test composition is toxic, what type of toxicities, and how toxic it would be as compared to the other known toxic compositions.

For the purpose of practicing the invention, the predictions of toxicity of the test composition based on its molecular profiles in LSCs does not have to be 100% accurate. To have a major positive impact on the efficiency and costs of drug development, one only has to modestly increase the probability that the less toxic and thus more successful drug candidates are, for example, on the top half of a prioritized list of new drug leads.

As noted in previous sections, alterations in gene or protein expression in LSCs exposed to a chemical composition can be detected by any of a number of means known in the art. Protein expression determined by MS is particularly convenient for such comparisons since the output data is typically fed directly into a computer connected to the mass spectrometer and is immediately available for a variety of calculations. If the alterations are susceptible to graphical representation, as when MS is used as the means of detection, a direct comparison can be made of the effect of the chemical composition on the expression of proteins compared to the control LSCs. If the alterations are detected by, for example, an ELISA, which produces a numerical readout, then the numerical readouts can be used to quantitate the expression of the protein. For gene expression, Northern blots can be correlated to the amount of RNA present for each RNA probed. Where gene expression is detected by hybridization arrays, the pattern of hybridization for nucleic acids from the test and control LSCs provides a basis for comparison.

The comparison of molecular profiles can be done by a number of means known in the art. Usually, the graphs resulting from the calculations can be stored, for example, in file folders or the like, and examined visually to discern common patterns of expression compared to the control, as well as differences. Conveniently, however, the data can be stored on and compared by a computer. Programs are available, for example, to compare mass spectrometry data. One form of comparison is based on the use of "subtractive calculation" and graphical representation to compare protein expression in the control LSCs ("control samples") against that of the LSCs contacted with test chemical composition(s) ("test samples"). In this type of comparison, the amount of each protein expressed by the control samples is subtracted from the amount expressed by the test samples. The control sample value is represented by a horizontal line, and any protein expressed in a different amount is represented as a line above or below the line (represensting positive and negative amounts compared to the control, respectively), with the height of the line designating the amount by which the expression of the test sample is different from that of the control. This method focuses attention on the differences in protein expression. In a like manner, the program can also be used to compare the expression of two or more test samples so that any differences in expression patterns can be readily discerned. It is expected that the more similar the pattern of expression, the more similar will be the effect, and the type of toxicity, of the two agents.

This form of comparison is further illustrated in FIG. 1, which is provided solely for clarity of discussion. FIG. 1 illustrates differences in nuclear proteins expressed by the LSCs. The top panel, panel 1A, is a half-tone reproduction of the readout from a mass spectrometer. Viewing the sheet from along the long axis, the top band would be the mass spectrum for the control, the LSCs grown in the absence of test chemical compositions, the middle band would be the spectrum for the LSCs grown in the presence of an added test chemical compound (test composition I), and the bottom band of FIG.

1A would be the mass spectrum of nuclear proteins expressed by LSCs exposed to a second test chemical compound (test composition II).

FIGS. 1B and 1C graphically illustrate differences in protein expression level between LSCs contacted with one of the test chemical compositions ("test LSCs") and control LSCs grown in standard tissue growth medium without added chemical compositions. These panels illustrate computational subtractions of identical proteins between the respective test LSCs and the control LSCs to indicate only those proteins which are significantly different in expression between the test and the control LSCs. Each bar represents a single protein and the length of the bar represents the amount of protein expressed by the LSCs exposed to the test composition compared to the amount expressed by the control LSCs. A bar above the center line indicates that the test LSCs express more of that protein than do the control LSCs; a bar below the line indicates that the test LSCs express less of that protein.

FIG. 1B illustrates differences in the nuclear proteins expressed by LSCs grown in the presence of test composition I compared to control LSCs. FIG. 1C illustrates the differences in the nuclear proteins expressed by the LSCs grown in the presence of test composition II, and the control. (Both the test and the control LSCs would be at the same time point of differentiation/development/growth.) In these illustrative figures, reading FIGS. 1B and 1C from the left, the first bar encountered is above the line at the same position for both Figures, but the height of the bar is much greater in FIG. 1C. This indicates that both groups of test LSCs express more of this protein than do the control, but that the cells contacted with test composition II express considerably more than do cells contacted with test composition I.

Continuing along the X, or molecular weight, axis of FIG. 1C, the next four bars encountered are shown to have a counterpart in FIG. 1B. Moreover, in each of the figures, the bars representing the same three proteins are below the line, whereas the bar for the same fourth protein is above the line. Once again, the height of the lines differs between FIGS. 1C and 1B. Thus, in this illustration, for the first 5 nuclear proteins detected, the LSCs contacted with test chemical compositions I and II are shown to display the same pattern of protein expression, but at different levels of expression. Each of these proteins, and the overall expression pattern, would be a candidate for inclusion in a profile indicating that an unknown chemical composition, such as a new potential therapeutic, had the tissue toxicity of the test composition(s). Conversely, the first protein detected as illustrated in FIG. 1C to the right of the 4000 Daltons molecular weight line is shown as not having a counterpart (or at least a counterpart in terms of being expressed at a level different from that of the control cells) in FIG. 1B. This protein would not be considered a protein that demonstrated a common pathway of tissue/organ toxicity of the test chemical composition(s). Depending on its correlation with expression pathways of other toxins against the same tissue/organ, it might, however, be associated with toxicity towards the same tissue/organ exhibited by the test chemical compositions. Similar analyses can be made for the other proteins illustrated on the two graphs.

Figure 2:
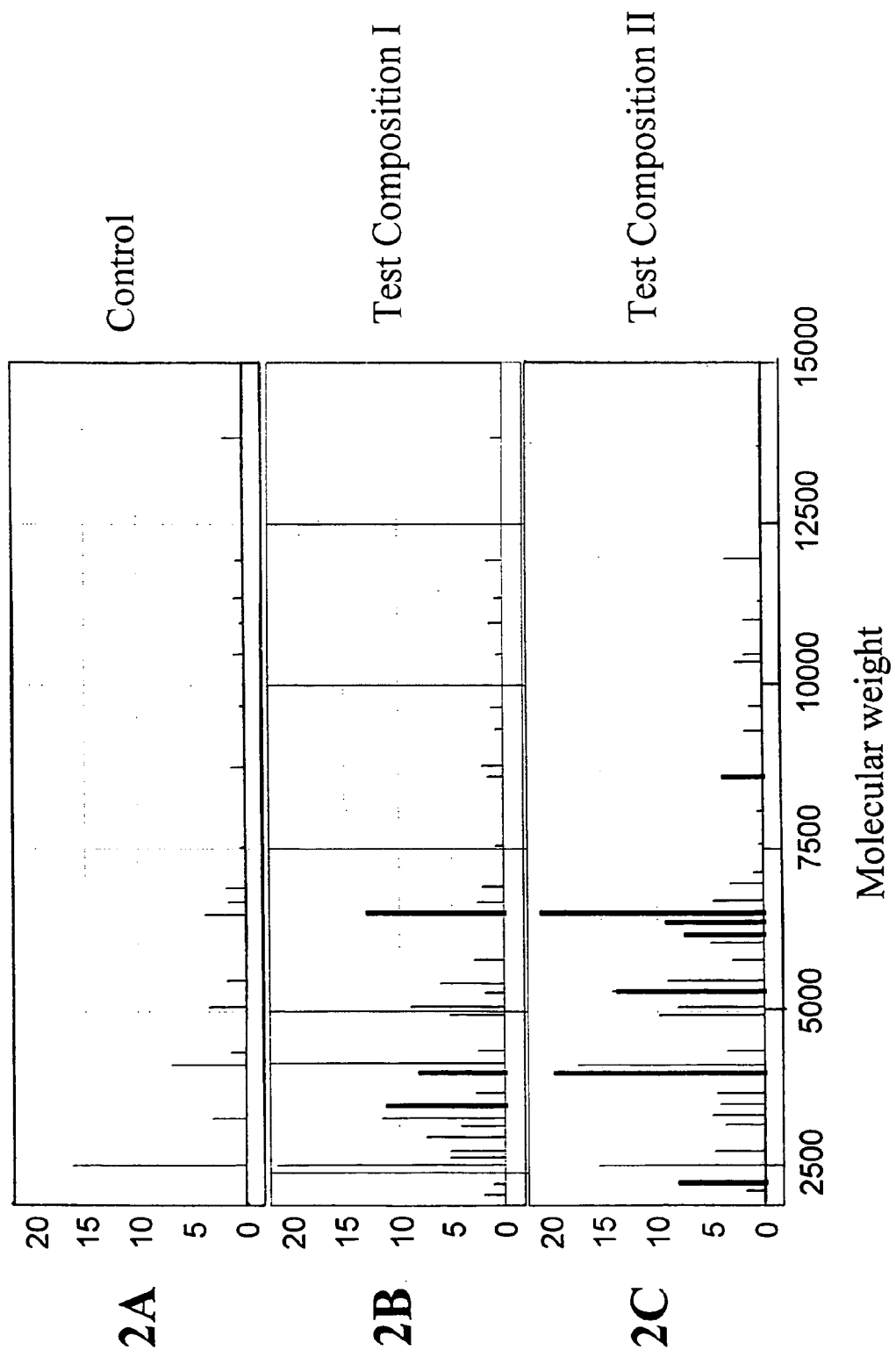
FIG. 2 is a bar graph illustrating expression of small nuclear proteins detected by mass spectrometry. X-axis: mass of protein detected. Y-axis: amount of protein detected, in relative units.
Figure 3:
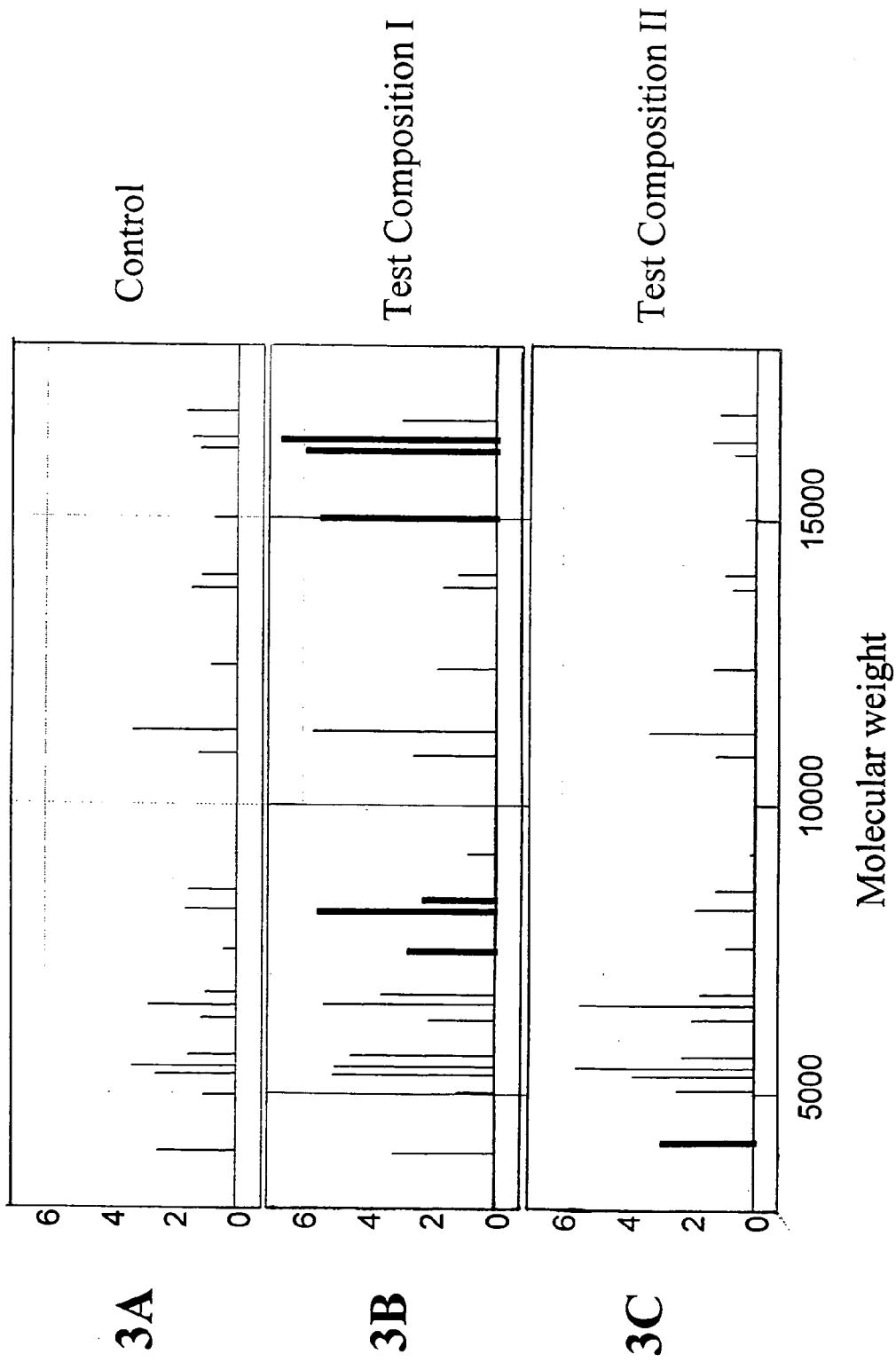
FIG. 3 is a bar graph illustrating expression of small cytoplasmic proteins detected by mass spectrometry. X-axis: mass of protein detected. Y-axis: amount of protein detected, in relative units.
Figure 4:
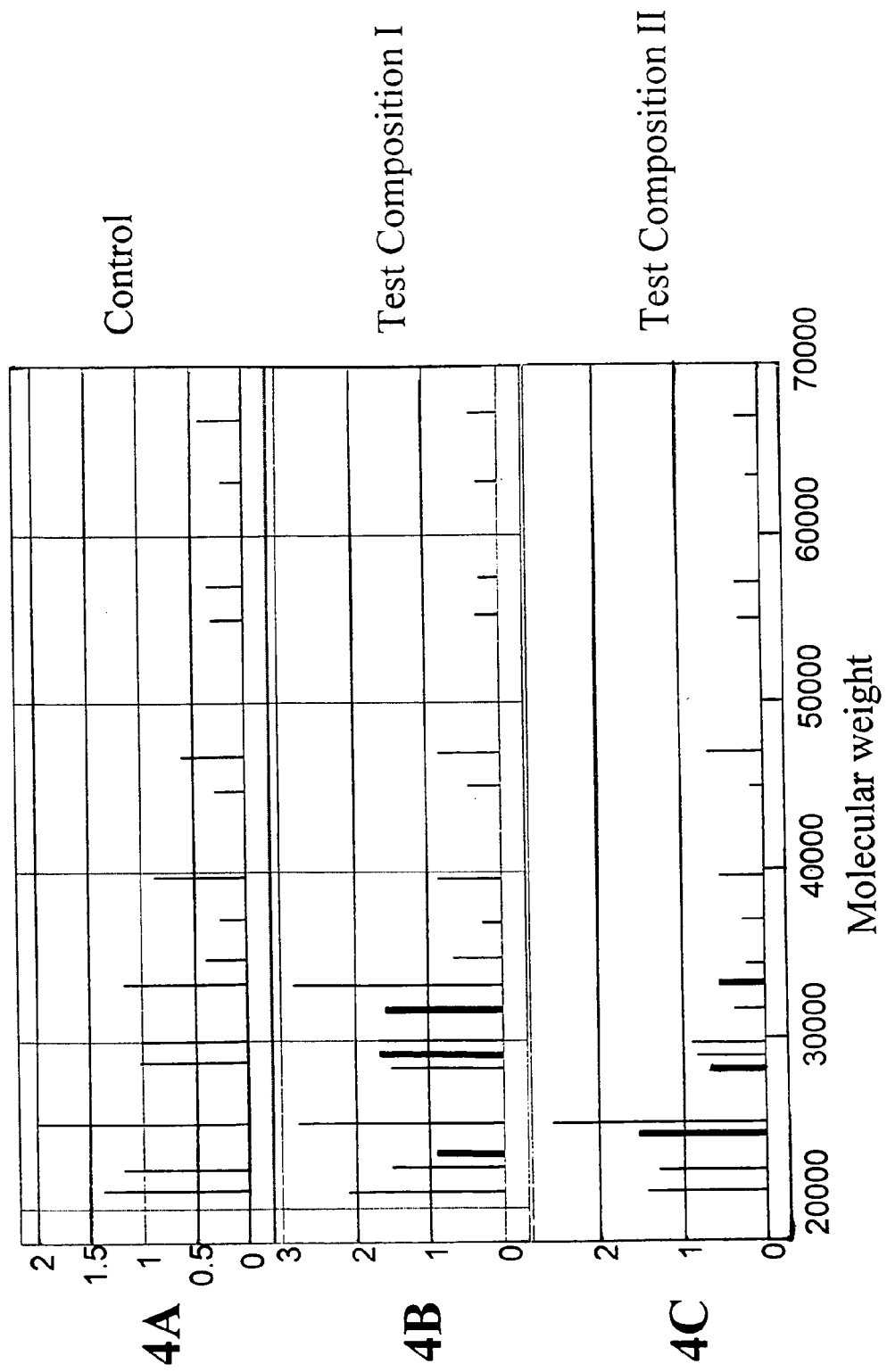
FIG. 4 is a bar graph illustrating expression of large nuclear proteins detected by mass spectrometry. X-axis: mass of protein detected. Y-axis: amount of protein detected, in relative units.

Another form of comparison is illustrated in FIGS. 2, 3 and 4, which are provided solely for clarity of discussion. These figures graphically depict the small nuclear, small cytoplasmic, and large cytoplasmic proteins expressed by control samples and by test samples exposed to one of two chemical compositions, as well the amount of the protein expressed by the samples. These graphs can be compared visually, and the proteins and the amounts expressed recorded manually. FIG. 2 compares the expression of small nuclear proteins in the three LSC groups described above. In these graphs, each bar in a panel represents a single protein, but the length of the bar represents the relative amount of protein expressed, rather than a comparison of the amount expressed compared to the control LSCs. In FIG. 2, the top panel, 2A, graphs the level of protein expression, as determined by mass spectroscopy, in the LSCs not exposed to chemical compositions in addition to those in a standard tissue culture medium. The middle panel, 2B, illustrates the level of expression of proteins of LSCs exposed to test composition I. And the bottom panel, 2C, illustrates the level of expression of LSCs contacted with test composition II. In these panels, the expression level of the protein, shown plotted on the Y axis as a relative value, is plotted against the molecular weight, shown plotted on the X axis. A visual comparison of the panels as illustrated reveals that some of the proteins expressed by the LSCs exposed to the two chemical compositions tested are the same, although perhaps at different levels of expression, and that others are different, and that both reveal a different pattern of expression than do the control LSCs not exposed to either composition.

FIG. 3 illustrates the level of expression of small cytoplasmic proteins in the same three groups of LSCs as those discussed in the preceding paragraph. The panels are arranged in the same order as in FIG. 2. Once again, the expression level of the protein for each group, shown plotted on the Y axis, is plotted against the molecular weight of the proteins, shown plotted on the X axis. Once again, a visual comparison of the panels as illustrated reveals that some of the proteins expressed by the LSCs exposed to the two chemical compositions tested are the same, although perhaps at different levels of expression, and that others are different.

Similarly, FIG. 4 illustrates a graphical analysis of the large cytoplasmic proteins expressed by the same groups of LSCs discussed above. Once again, the level of expression determined by the mass spectrometry is plotted on the Y axis, while the molecular weight is plotted on the X axis. Once again, clear similarities, and clear differences, can be observed between the protein expression patterns of the LSCs exposed to the test chemical compositions, and between those protein expression patterns and that of the LSCs grown without exposure to either of the test chemical compositions.

It would be clear from figures such as the above that the drugs can induce complex and unique protein expression patterns. Some proteins would be expressed in smaller amounts (or "down regulated") compared to the protein expression in the control LSCs, and others would be expressed in higher amounts (or "up regulated") compared to the controls. Additionally, the chemical compositions may affect some of the same proteins and thus share common sub-patterns.

For example, as illustrated. in FIG. 2C, to the right of the line denoting a molecular weight of 2500 Daltons, there is shown a tall line, over 15 units on the Y axis, which would designate a strongly expressed protein. Following the line up to panels 2B and 2A, it is shown that that same protein is expressed at high levels in both the LSCs contacted with a test composition I and in the control LSCs not contacted with either composition. This protein, therefore, would be deemed as highly expressed in LSCs at the point in development at which the samples are taken, although there would be some variation in level of expression. Continuing to the right in panel 2C and making the same comparisons, however, the next protein present is also shown as present, in approximately the same amount, in the LSCs exposed to test composition I, but is not expressed at all by the control LSCs. Thus, this protein would be a candidate for differentiating chemical compositions with the tissue/organ toxicity of the test chemical composition(s) from other compositions and other kinds of toxicity.

Preferably, the results are placed into a computer database, with information about the known toxicities of the chemical compositions recorded in searchable data fields. Entries of data from other forms of detecting alterations in protein or gene expression can also be reviewed and recorded manually or in a computer database. For example, the values from an ELISA, or the proteins identified on a Western blot can be recorded to identify the types and amounts of proteins expressed in control and test samples. Similarly, the patterns on a Northern blot, or the hybridization pattern on an oligonucleotide array, can be recorded to identify the gene expression of control and test samples. The information can be kept manually, but preferably is maintained in a computer searchable form.

Standard database programs, such as Enterprise Data Management (Sybase, Inc., Emeryville, Calif.) or Oracle8 (Oracle Corp., Redwood Shores, Calif.) can be used to store and compare information. Alternatively, the data can be recorded, or analyzed, or both, in specifically designed programs available, for example, from Partek Inc. (St. Charles, Mo.).

Additionally, companies selling integrated analytical systems, such as mass spectrometers, provide with the machines integrated software for recording results. Such companies include Finnigan Corp. (San Jose, Calif.), Perkin-Elmer Corp. (Norwalk Conn.), Ciphergen Biosystems, Inc. (Palo Alto Calif.), and Hewlett Packard Corp. (Palo Alto, Calif.). Similarly, companies such as Affymetrix, Inc. (Santa Clara, Calif.) and Incyte Pharmaceuticals, Inc. (Palo Alto Calif.) providing oligonucleotide hybridization services maintain proprietary image recognition algorithms to record and analyze the scanned images of hybridization arrays.

In a preferred embodiment, the data can be recorded and analyzed by neural network technology. Neural networks are complex non-linear modeling equations which are specifically designed for pattern recognition in data sets. One such program is the NeuroShell Classifier™ classification algorithm from Ward Systems Group, Inc. (Frederick, Md.) a classification algorithm optimized to solve classification and categorization problems. Other neural network programs are available from, e.g., Partek, Inc., BioComp Systems, Inc. (Redmond Wash.) and Z Solutions, LLC (Atlanta, Ga.).

H. Adapting Array Readers

In one embodiment, the invention relates to the formation of arrays of hybridized oligonucleotides or of bound proteins to detect changes in gene or protein expression, respectively. Such arrays can be scanned or read by array readers.

Typically, the array reader will have an optical scanner adapted to read the pattern of labels on an array, such as of bound proteins or hybridized oligonucleotides, operably linked to a computer which has stored on it, or accessible to it (for example, on an external drive or through the internet) one or more data files having a plurality of gene expression or protein expression profiles of mammalian LSCs contacted with known or unknown toxic chemical compositions. The array reader can, however, be adapted with a detection device suitable to "read" labels that can not be read optically, such as electronic transponders.

I. Use in High Throughput Screening

The methods of the invention can be readily adapted to high throughput screening. High throughput ("HTP") screening is highly desirable because of the large number of uncharacterized compounds already developed in the larger pharmaceutical companies, as well as the flood of new compounds now being synthesized by combinatorial chemistry. Using the invention, hundreds of chemical compositions can be tested on LSCs and the resulting alterations in gene or protein expression, or both, compared to toxicities of known chemical compositions to predict the type and possibly the degree of toxicity the new compounds possess. Those compositions with acceptable toxicity profiles can then be considered for further levels of testing.

HTP screening can be facilitated by using automated and integrated culture systems, sample preparation (protein or RNA/cDNA), and analysis. These steps can be performed in regular labware using standard robotic arms, or in more recently developed microchip and microfluidic devices, such as those developed by Caliper Technologies Corp. (Palo Alto, Calif.), described in U.S. Pat. No. 5,800,690, by Orchid Biocomputer, Inc. (Princeton, N.J.), described in the Oct. 25, 1997 New Scientist, and by other companies, which provide methods of automated analysis using very low volumes of reagents. See, e.g., McCormick, R., et al., Anal. Chem. (1997), 69:2626-2630; Turgeon, M., *Med Lab. Management Rept*, December 1997, page 1.

EXAMPLES

Example 1

Selecting Chemical Compounds For Toxicity Screening

Compositions that fall into particular categories of toxicity are used to establish molecular profiles and compile libraries for particular toxicities. Table 1 lists a number of compositions that are known to be toxic to certain tissues or organs or during developmental stages. In particular, those compositions that cause liver toxicities are assessed for their molecular profiles by determining alterations of gene or protein expression patterns in LSCs contacted by each composition. A library comprising molecular profiles of compositions having liver toxicities is therefore compiled. Those compositions causing cardiovascular toxicities are similarly assessed for their molecular profiles and a library compiled. In addition, molecular profiles and library thereof for compositions having toxicities on the central nervous system and for compositions having developmental toxicities are similarly established using the LSC system. The experimental procedures as described above in general, and in more detail in the following examples, are followed to compile the molecular profiles and libraries for compositions with particular type of toxicities.

Drugs with known or suspected of having activities against particular diseases can be used to establish molecular profiles and libraries for toxicity assessment. Antineoplastic drugs with similar toxicities, for example those listed in Table 1, can be used to compile molecular profiles by determining the alterations in gene or protein expression patterns in LSCs exposed to these drugs. Similarly, antibiotics with similar toxicities can also be assessed for their alterations in gene or protein expression patterns in LSCs. Also used are drugs controlling diabetes, drugs for lowering lipid levels, or anti-inflammatory drugs. Once a composite library comprising molecular profiles of specific type of drugs having similar toxicities is established, it can be used to screen for new drug leads of the similar type for their potential toxicities. Again, the experimental procedures as described above in general, and in more detail in the following examples, are followed for compiling molecular profiles and libraries, and for typing/ranking toxicities of new drug leads.

Example 2

Establishing Protein Profiles For Chemical Agents Relating to Tissue/Organ Toxicities This Example demonstrates the culturing of liver stem cells, the exposure of the liver stem cells to different chemical agents having pre-determined tissue or organ toxicities, and the determination of changes in protein expression in the liver stem cells.

Isolation of Cells

Human liver progenitor cells are isolated, purified and culture-expanded according to methods described below:

Method 1:

Liver precursor cells are isolated according to Reid et al., U.S. Pat. Nos. 5,576,207 and 5,789,246. Briefly, a liver section is placed in an ice-cold PBS solution that contain 500-5000 mg/L glucose, and 2-10% antibiotics (e.g., penicillin and streptomycin). The liver section is minced and sequentially digested with a solution containing collagenase, pronase and deoxyribonuclease, prepared in a saline solution containing 1 mM $CaCl_2$. Digestion is done at 37° C. in a shaking water bath for about 20 minutes. The partially digested tissue is then strained through a tissue sieve by gravity and the undigested remnants are re-digested two times. Collected cells are then washed with saline solution. Cells are plated on or in a matrix of collagen Type IV so as to allow them to polarize and feed through a basal surface such as a Millicell support. Matrix-bound cells are provided with an embryonic liver-derived stromal cell feeder layer, and cultured in a basal medium (e.g., RPMI 1640, Ham's F10, Ham's F12) containing less than 0.4 mM calcium and 10 µg/ml insulin, 10 µU/ml growth hormone, 20 mU/ml prolactin, 10 µg/ml glucagon, 50 ng/ml EGF, $10^{-8}$M dexamethasone, $10^{-9}$M T3, $3\times10^{-10}$M selenium, $10^{-7}$M copper and $10^{-10}$M zinc (medium containing the foregoing is hereinafter referred to as "medium A"). Alternatively, the medium further contains 0.4% bovine serum albumin, 76 mEq per liter of free fatty acid mixture having 31% palmitic acid, 2.8% palmitoleic acid, 11.6% stearic acid, 13.4% oleic acid, 35.6% linoleic acid and 5.6% linolenic acid (medium containing the foregoing is hereinafter referred to as "medium B"). Medium A or B containing $10^{-4}$M dexamathasone, 0.1 to 100 µg/ml insulin, 50 ng/ml multi-stimulating activity (Sigma Chemical Co. St. Louis, Mo.), 25 to 100 ng/ml EGF, $10^{-4}$M norepineph-rine, 25 µl/ml hepatopoietins and 10 ng/ml FGF's, can also be used. Liver precursor cells obtained by this method are analyzed according to the present invention as described below.

Method 2:

Hepatoblasts are isolated according to the methods described in Reid et al., U.S. Pat. No. 6,069,005. Briefly, livers are dissected from rat fetuses of gestational day 14, and placed in fresh ice-cold Hank's Salt Solution (HBSS). After all tissues are collected and non-hepatic tissue removed, HBSS-5 mM EGTA is added to a final EGTA concentration of 1 mM. Livers are then gently triturated 6 to 8 times to partially disaggregate the tissue and then centrifuged at 400 g for 5 minutes at 4° C. All subsequent centrifugation steps are performed at the same settings. Supernatant is removed and the pellet of cells and tissue resuspended in 0.6% collagenase D (Boehringer Mannheim, Indianapolis, Ind.) in HBSS containing 1 mM $CaCl_2$, gently triturated and then stirred at 37° C. for 15 minutes. The dispersed cells are pooled, suspended in HBSS containing 1 mM EGTA and filtered through a 46 µm tissue collector (Bellco Glass, Inc., Vineland, N.Y.). The cell suspension is centrifuged and cells resuspended in HBSS supplemented with MEM amino acids, MEM vitamins, MEM non-essential amino acids, insulin (10 µg/ml), iron-saturated transfernin (10 µg/ml), free fatty acids (7.6 mEq/L), trace elements, albumin (0.1%, fraction V, fatty acid free, Miles Inc., Kankakee, Ill.), myo-inositol (0.5 mM) and gentamicin (10 µg/ml, Gibco BRL, Grand Island, N.Y.) (HBSS-MEM). Cell number and viability are determined by hemacytometer and trypan blue exclusion.

To remove erythroid cells, panning dishes prepared according to standard procedure with a rabbit anti-rat RBC IgG (Rockland Inc., Gilbertsville, Pa.) are used. Antibodies (0.5 mg/dish) diluted in 0.05M Tris pH 9.5 are poured on 100 $mm^2$ bacteriological polystyrene petri dishes (Falcon, Lincoln Park, N.J.). The dishes are swirled to evenly coat the surface and incubated at room temperature for about 40 minutes. Coated dishes are washed four times with PBS and once with HBSS containing 0.1% BSA prior to use.

Cell suspension containing up to $3\times10^7$ cells are incubated at 4° C. for about 10 minutes in the dishes coated with the rabbit anti-rat RBC IgG. Non-adherent cells are removed by aspiration and the plates washed three times with HBSS-0.1% BSA-0.2 mM EGTA and centrifuged. The cell pellet is resuspended in HBSS-MEM, and RBC panning repeated. Following the second RBC panning, cell number and viability are determined again.

Cells recovered after RBC panning are then labeled in suspension by incubating with mouse monoclonal antibody OX-43 (1/200=15 µg/ml, MCA 276, Bioproducts for Science, Indianapolis, Ind.) and monoclonal antibody 374.3 (1/500-1/750, available from R. Faris and D. Hixon, Brown University, Providence, R.I.) simultaneously at 4° C. for 40 minutes. Secondary antibodies are PE-conjugated anti-mouse IgG, heavy chain specific (Southern Biotechnology Inc., Ala.) and FITC-conjugated anti-mouse IgM, heavy chain specific (Sigma Chemical Co., St. Louis, Mo.).

Cells before and after sorting are maintained at 4° C. and in HBSS-MEM. After antibody labeling, propidium iodide at 10 µg/ml is added to each sample. Fluorescence activated cell sorting is performed with a Becton Dickinson FACSTAR+ (San Jose, Calif.) using a 4 W argon laser with 60 mW of power and a 100 µm nozzle. Fluorescent emission at 488 nm excitation is collected after passing through a 530/30 nm band pass filter for FITC and 585/42 nm for PE. Fluorescence measurements are performed using logarithmic amplification on biparametric plots of FL1(FITC) vs. FL2 (PE). Cells are considered positive-when fluorescence-is greater than 95% of the negative control cells.

For measurement of physical characteristics of cells, FACSTAR+ pararneteres are FSC gain 8 and SSC gain 8. HBSS is utilized as sheath fluid. List mode data are obtained and analyzed using LysisII software.

To determine positivity to a single antibody dot plots of fluoresnce vs. side scatter are used. Density plots FL1 vs. FL2 are used to select populations with respect to expression of both antigens. A sort enhancement module is used for non-rectangular gating and use of multiparametric gating to select populations of interest.

Sorted cells from all populations are plated in a serum-free, hormonally-defined medium with α-MEM as the basal medium to which the following components are added: insulin (10 µg/ml); EGF (0.01 µg/ml, Upstate Biotechnology, Lake Placid, N.Y.); growth hormone (10 µU/ml); prolactin (20 mU/ml); Triiodothyronine ($10^{-7}$M); dexamethasone ($10^{-7}$M); iron saturated transferrin (10 µg/ml); folinic acid ($10^{-8}$M, Gibco BRL, Grand Island, N.Y.), free fatty acid mixture (7.6 mEq/L; Nu-Chek-Prep, Elysian, Minn.); putrescine (0.02 µg/ml); hypoxanthine (0.24 µg/ml); thymidine (0.07 µg/ml); bovine albumin (0.1%, fraction V, fatty acid free, Miles Inc. Kankakee, Ill.); trace elements; $CuSO_4.5H_2O$ (0.0000025 mg/l), $FeSO_4.7H_2O$ (0.8 mg/l), $MnSO_4.7H_2O$ (0.0000024 mg/l), $(NH_4)_6Mo_7O_2 \cdot 4H_2O$ (0.0012 mg/l), $NiCl_2.6H_2O$ (0.000012 mg/l), $NH_4VO_3$ (0.000058 mg/l), $H_2SeO_3$ (0.00039 mg/l); Hepes (31 mM) and Gentamicin (10 µg/ml, Gibco BRL, Grand Island, N.Y.) [HDM]. Reagents are supplied by Sigma Chemical Company, St. Louis, Mo., unless otherwise specified. The trace element mix is available from Dr. I. Lemishka, Princeton University, N.J.

Aliquots of each cultured population as well as cytospins of various cell suspensions are fixed with ice-cold ethanol or acetone. After blocking with PBS containing 1% BSA for 30 minutes at room temperature, the fixed cells are studied by indirect immunofluorescence using the following primary antibodies: polyclonal rabbit-anti-rat albumin (United States Biochemical Corporation, Cleveland, Ohio), rabbit-anti-mouse AFP antiserum (ICN Biomedical, In., Costa Mesa, Calif.), monoclonal mouse-anti-human cytokeratin 19 (Amersham Life Science, Arlington Heights, Ill.), polyclonal rabbit-anti-human IGF II receptor (Dr. Michael Czech, University of Worchester, Mass.), mouse monoclonal. anti-rat-Thy-1 (OX-7, Bioproducts for Science, Indianapolis, Ind.), monoclonal mouse-anti-desmin (Boehringer Mannheim, Indianapolis, Ind.), and 258.26, a monoclonal mouse-anti-rat antibody identifying postnatal hepatocytes as well as some fetal liver parenchymal cells (Drs. R. Faris and D. Hixon, Brown University, RI). Second antibodies include species specific Rhodamine conjugated antibodies corresponding to the primary antibodies. Negative controls consist of cells stained with mouse or rabbit IgG or mouse isotype controls. Freshly isolated adult hepatocytes are used as positive controls for albumin staining. Gamma-glutamyltranspeptidase (GGT) is assayed by immunochemistry on ethanol fixed cells using the method described by Rutenberg et al., *J. Hist. Cyt.* (1969), Vol. 17, pp. 517-526.

The cell population containing primarily immature, progenitor liver cells is identified as the population expressing albumin, alpha-fetoprotein and GGT. In some instances, the identity of the cells are confirmed by Northern and/or Western blot analysis for markers of these cells, which are described herein and known in the art.

The liver progenitor cells obtained are maintained in HDM and analyzed according to the present invention as described below.

Method 3:

Livers are dissected from rat fetuses at day 15 of gestation and placed into ice-cold, $Ca^{2+}$-free HBSS containing 0.8 mM $MgCl_2$, 20 mM HEPES, pH7.3 and gently agitated at room temperature for about 1 minute. After removal of non-hepatic tissue, livers are gently triturated and then stirred at 37° C. for about 10-15 minutes with 0.6% type IV collagenase (Sigma Chemical Co., Lot 11H6830, St. Louis, Mo.) in HBSS containing 1 mM $CaCl_2$ and 0.06% DNAse I (Boehringer Mannheim, Indianapolis, Ind.). At 5 minute intervals, tissue fragments are allowed to sediment at 1 g. Supernatant is recovered and fresh collagenase solution added. The dispersed cells are pooled, suspended in HBSS containing 5 mM EGTA and filtered through a 46 µm tissue collector (Bellco Glass, Inc., Vineland, N.Y.) under 1 g. The resultant cell suspension is centrifuged at 4° C. for about 5 minutes under 450 g. The cell pellet is resuspended in HBSS containing 0.2 mM EGTA and 0.5% BSA (HBSS-EGTA-0.5% BSA), and the cell number is estimated. Cell viability is assessed by exclusion of 0.04% trypan blue, and an aliquot of the suspension is centrifuged at 450 g for about 5 minutes.

To immunoadhere hemopoietic and endothelial cells onto antibody-coated polystyrene dishes, panning dishes are prepared according to standard procedures with rabbit anti-rat RBC IgG (Inter-cell Technologies, Inc;, Hopewell, N.J.) and goat IgG directed towards mouse whole IgG molecule (M-3014, Sigma, St. Louis, Mo.). Antibodies (0.5 mg/dish) diluted in 0.05M Tris pH 9.5 are poured on 100 mm² bacteriological polystyrene petri dishes (Flacon, Lincoln Park, N.J.) to evenly coat the surface and incubated at room temperature for about 40 minutes. Coated dishes are washed with PBS and then HBSS containing 0.1% BSA prior to use.

Cell suspension containing up to $3 \times 10^7$ cells is incubated at 4° C. for 10 minutes in the coated dishes. Supernatant containing non-adherent cells is removed by gentle aspiration while tilting and swirling, combined with washes of HBSS-EGTA-0.1% BSA, and centrifuged at 4° C. for about 5 minutes under 450 g. Cells are pooled and repanned with a fresh dish coated with rabbit anti-rat RBS IgG. Non-adherent cells are then removed as above and resuspended with HBSS-EGTA-0.5% BSA to a concentration of $1 \times 10^7$/ml. The enriched hepatoblasts are then incubated simultaneously at 4° C. for 40 minutes with mouse monoclonal antibody OX-43 (15 µg/ml, MCA 276, Serotec, Indianapolis, Ind.). After washing, enrichment for hepatoblasts is achieved by panning cells at 4° C. for 10 minutes in a dish coated with the goat anti-mouse whole IgG antibody. Non-adherent cells are removed as above.

The liver progenitor cells obtained are maintained in HDM (see method. 3 above) and analyzed according to the present invention as described below.

Method 4:

Liver progenitor cells are isolated according to the methods described in Naughton et al., U.S. Pat. No. 5,559,022. Briefly, liver is removed from adult rats according to standard procedures. The liver is placed on a modified Buchner funner and perfused with a buffer containing $Ca^{2+}$ and 0.05 g/dl type IV collagenase (Sigma Chemical Co., Mo.) in a recirculating system for about 15-20 min. The liver is then transferred to a Petri dish containing collagenase buffer supplemented with 1.5% BSA and the hepatocytes are liberated into suspension after the perforation of Glisson's capsule, filtered through a 185 µm nylon sieve, pelleted by centrifugation, and resuspended in complete medium, DMEM conditioned with 6% fetal bovine serum and 10% equine serum and supplemented with 35 µl glucagon (Sigma #G9261), 10 µg insulin (Sigma #14011), 0.25 g glucose, and 250 µl hydrocortisone hemisuccinate per 500 ml of medium. Hepatic cells are separated into subpopulations using Percoll gradient centrifugation.

To obtain liver progenitor cells, a population of large (about 30 ||m in diameter), acidophilic cells which proliferate and differentiate in culture to cells resembling mature hepatocytes is separated as follows: single cell suspensions of freshly isolated liver cells are centrifuged (500×g/5 min) and the pellet is resuspended in medium. The cell suspension is layered over 25 ml of a 70% v/v solution of 'neat' Percoll and 1XPBS and centrifuged at 800×g for 10 min. The two lower zones (of 4) are pooled, washed, and centrifuged against 25%/50% (v/v/,neat Percoll/1XPBS) discontinuous gradient yielding a distinct interface zone and a pellet. The interface (density=1.0381 g/ml) consists of about 90% large, lightly acidophilic, mono- or binuclear cells with multiple, prominent nucleoli. Liver precursor cells obtained by this method are then analyzed according to the present invention as described below.

Method 5:

Liver progenitor cells are isolated according to the methods described in Faris, PCT Publication WO00/03001. Briefly, liver is excised, minced and placed in a suspension buffer containing HBSS with 0.1 M Hepes. The minced tissue is incubated at 37° C. on a stirring plate for about 40-50 minutes. The combined suspension is sequentially filtered through a 230 micron steel mesh filter, and a 60 micron nylon mesh filter. Remnants remaining on the filters are washed off and placed in digestion buffer, which is a CMF media (Gibco) solution containing 0.02 g of bovine serum albumin, 0.1M Hepes, $CaCl_2$ (500 mM), STI (0.025 g/100 ml; Gibco), and collagenase Type IV (60 units/ml), @pH 7.4-7.5. Cells are incubated at 37° C. in a shaker water bath. After 20 minutes, the cell suspension is removed to a tube and allowed to settle by gravity.

The supernatant and the remnant (settled material) are then separated. The supernatant is decanted and centrifuged at 80 ×g for 5 minutes. Fresh digestion buffer is added to the cells and the cells placed back in the shaking water bath. The pellet remaining after the centrifugation is resuspended with washing buffer (DMEM-F12 and BSA (1 g/100 ml), @pH 7.2-7.3.

The cell suspension is filtered through a 60 micron nylon mesh filter and then mixed with an equal volume of 90% Percoll and 10% 10×DMEM-F12. This is centrifuged at 300 ×g for about 5 minutes. The pellet is resuspended in washing buffer (as described above), and centrifuged at 120 ×g for about 5 minutes. The pellet is then resuspended in washing buffer.

Dynabeads conjugated to a mouse monoclonal antibody specific for rat bile duct and mesothelial cells ($IgG_{2b}$) are added to the cell suspension, and incubated at 4° C. on a rotator for about 10 minutes. The suspension is then placed on a magnet to remove antibody-positive cells, which are discarded. This step is repeated at least 3 more times. The antibody-negative cells are subjected to more incubations with Dynabeads conjugated to an antibody specific for CCAM (e.g., anti-rat cell-CAM 105; Endogen), and antibody-positive cells with a stem cell attached (e.g., cell clusters such as doublets and triplets) are cultured and cytospinned.

Isolated cell clusters are trypsinized to dissociate the cell clusters, then exposed to antibodies specific for cell markers such as CK19 (Amersham), CCAM (Endogen), dipeptidyl peptidase-4 (Endogen) in combination with magnetic beads or FACS sorting to enrich for the stem cells.

Liver precursor cells obtained by this method are analyzed according to the present invention as described below.

Exposure of Cells to Test Chemical Composition and Methods of Analysis of Protein Eexpression Cells isolated as described above are plated at high density (e.g., 50,000 to 100,000 cells/$cm^2$ per well) in wells coated with type I collagen extracted from rat tail tendon, to allow differentiation of cells. A drug with pre-determined toxicity, such as troglitazone, which is a drug designed for the control of diabetes which has shown rare but severe liver toxicity and recently removed from the market, is added at a final concentration of about 20 µM to one group of plates (group "A") containing the LSCs. On the same day, another drug with pre-determined toxicity, such as erythromycin estolate (Sigma, catalog number E8630), which is a form of erythromycin with known liver toxicity, is added to a second group of plates (group "B") at a final concentration of about 50 µM. A third group of plates containing the cultured cells (group "C1") is cultured without any added drugs to serve as a control. Additionally, plates containing only tissue culture medium (group "C2") are cultured alongside those containing cultured cells as a control for degradation of proteins in the culture medium. Following a period of exposure of the cells to the drugs, for example after about ten, twenty, thirty and forty days, the cultures are harvested, the cells washed with a buffer such as PBS, and then lysed in a buffer that contains, for example, PBS, 0.5% Triton X-100 for about 10 minutes on ice. The nuclei are pelleted, and the supernatant removed and stored at −80° C. until analysis. The nuclei are lysed in a buffer such as PBS with 0.2% SDS and dounce homogenized to shear the DNA. The insoluble material is pelleted and the nuclear lysates stored at −80° C. until analyzed. Cytoplasmic and nuclear lysates are also taken on day zero prior to exposure to any test chemical compositions to serve as additional controls.

The lysates and medium samples are diluted by, for example, 3 fold in buffer containing 50 mM Tris-HCl at pH 8, and 0.4 M NaCl. Aliquoted samples of diluted lysate or medium are placed in a sizing spin column that fractionates the sample with a size cut-off of, for example, 30 kD and equilibrated in 50 mM Tris-HCl, pH 8 and 50 mM NaCl. The column is spun at an appropriate force and for an appropriate period, such as 700 g for 3 minutes, for each fraction. Multiple fractions of about 25 µL are collected for each column using the column equilibrated buffer.

The samples are partitioned by surface enhanced laser desorption/ionization ("SELDI"), and proteins are detected by mass spectroscopy. SELDI permits proteins to be captured on a surface of choice, which can then be washed at selected stringency, to permit fractionation according to desired characteristics such as affinity for metal ions of the surface used for capture.

Ciphergen normal phase chips (Ciphergen Biosystems, Palo Alto, Calif.) are used to partition the proteins in the fractions generated by the spin columns. Aliquots of about 1 µl of each fraction are deposited on a spot on the chip, and the sample is air dried at room temperature for about 5 minutes. A mixture of about 0.5 µL of saturated sinapinic acid ("SPA") in 50% acetonitrile with 0.5% trifluroacetic acid ("TFA") is applied to each spot. The chip is again permitted to air dry for about 5 minutes at room temperature, and a second aliquot of the SPA mixture is applied.

Chips are read by the Ciphergen Protein Biology System 1 reader. Exemplary reader settings are as follows. Auto mode is used for data collection, at the SELDI quantitation setting. Two sets of protein profiles are collected, one at low laser intensity (at 15 with filter out) and one at high laser intensity (at 50 with filter out), detector set at 10. An average of 15 shots per location on the same sample spot are made. Protein profiles from different lysates are compared using SELDI software (Ciphergen Biosystems, Palo Alto, Calif.). This program assumes two proteins with a molecular weight within about 1% of each other are the same. It then quantitates the results, compares the test samples against the control samples, and prints a graph showing the amount of each protein in the control as a horizontal line, with any reduction or excess in the amount of each protein in the test sample compared to the amount of that protein in the control sample as a line below or above the line representing the control.

Example 3

Screening Of Anti-cancer Drugs for Tissue and Organ Toxicities

This example illustrates using the LSC system for screening anti-cancer agents for their tissue or organ toxicities.

Compounds and drugs (both anti-cancer and therapeutic) that have known toxicities and biology endpoints in humans and/or animals are selected for compiling their gene or protein expression profiles in LSCs. In addition, compounds are selected with related known mechanisms of activities and with regard to compounds that have been used in previous studies to correlate clinical outcomes with human in vitro cell culture effects. Table 3.

TABLE 3

TOXICITIES

| DRUGS | DEV | LIVER | CV | GI | CNS | RENAL | BLOOD | MECHANISM |
|---|---|---|---|---|---|---|---|---|
| chloroquinoxaline sulfonamide | | | | | | | | ? |
| didemnin B | | | | | | | | ? |
| cyclosophosphamide | | | | | | | | alkylator |
| bizelesin | | | | | | | | alkylator |
| carboplatin | | | | | | | | alkylator |
| cisplatin | | | | | | | | alkylator |
| oxaliplatin | | | | | | | | alkylator |
| ecteinascidin 743 | | | | | | | | alkylator |
| penclomedine | | | | | | | | alkylator |
| methotrexate | | | | | | | | anti-metabolite |
| fuzarabine | | | | | | | | anti-metabolite |
| fludarabine | | | | | | | | anti-metabolite |
| flavopiridol | | | | | | | | CdK inhibitor |
| doxorubicin | | | | | | | | DNA intercalator |
| amonafide | | | | | | | | DNA intercalator |
| daunorubicin | | | | | | | | DNA syninhib |
| gemcitabine | | | | | | | | DNA syninhib |
| etoposide | | | | | | | | DNA syninhib |
| deoxyspergualin | | | | | | | | immunosuppression |
| camptothecin | | | | | | | | topo-I inhibitor |
| 9 aminocamptothecin | | | | | | | | topo-I inhibitor |
| topotecan | | | | | | | | topo-I inhibitor |
| merbarone | | | | | | | | topo-II inhibitor |
| dolastatin 10 | | | | | | | | tubulin inhibitor |
| taxol | | | | | | | | tubulin inhibitor |
| vinblastine | | | | | | | | tubulin inhibitor |
| vincristine | | | | | | | | tubulin inhibitor |
| vindesine | | | | | | | | tubulin inhibitor |
| vinorelbine | | | | | | | | tubulin inhibitor |

"Dev" = developmental
"GI" = gastro-intestinal
"CV" = cardiovascular
"CNS" = central nervous system a. Establishing Gene Expression Profiles The gene expression pattern of a selected compound is measured and quantified using cDNA microarrays and is normalized with cellular differentiation. The gene expression pattern of the compound is compared with a control LSC culture not exposed to the compound or, where appropriate, LSC cultures treated with related drugs with similar function or dose limiting toxicity. By compiling the gene expression profiles for a number of anti-cancer agents having similar or related toxicities, common alterations in gene expression are discerned and correlated with the toxicities, and are used as surrogate profiles for assessing the toxicities of test anti-cancer drug candidates.

The cDNA microarray can be any one of many kinds that are known and available in the art, for example, as described in Shalon et al (1996), *Genome Res* 6:639-645. cDNA microarrays allow for the simultaneous monitoring of the expression of thousands of genes, by direct comparison of control and chemically-treated cells. 3' expressed sequence tags (ESTs) are arrayed and spotted onto glass microscope slides at a density of hundreds to thousands per slide using high speed robotics. Fluorescent cDNA probes are generated from control and test RNAs using a reverse transcriptase reaction with labeled dUTP using fluors that excite at two different wavelengths, i.e. Cy3 and Cy5, which allows for the hybridization of both the control and test RNA to the sane chip for direct comparison of relative gene expression in each sample. The fluorescent signal is detected using a specially engineered scanning confocal microscope. A collection of 15,000 sequence verified human clones and 8700 mouse clones can be used in making cDNA microarrays. These microarrays are ideal for the analysis of gene expression patterns in LSC cultures treated with a variety of agents.

Another example of microarray analysis is described in Lockhart et al., U.S. Pat. No. 6,040,138. In this method, labeled RNA or cDNA from target cells are hybridized to a high density array of oligonucleotide probes where the high density array contains oligonucleotide probes complementary to subsequences of target nucleic acids in the RNA or cDNA sample. 20 mer oligonucleotide probes prepared as described in Lockhart et al., supra, are arrayed on a planar glass slide. Labeled RNAs are generated from control and test LSCs using methods known in the art, such as incubating cells in the presence of labeled nucleotides. Alternatively, labeled cDNAs are prepared from RNAs of the test and control cells using a reverse transcription reaction with labeled nucleotides, such as dUTP using fluors that excite at different wavelengths. Signal from the labeled RNA or cDNA can be read by a laser-illuminated scanning confocal fluorescence microscope. The microarray in this method is capable of simultaneous monitoring of more than 10,000 different genes.

Briefly, RNAs are isolated from control and treated LSCs. Total RNA are prepared using the RNAeasy kit from Qiagen. Subsequently, RNA are labeled either with Cy3 or Cy5 dUTP in a single round of reverse transcription. The resultant labeled cDNAs are mixed in a concentrated volume and hybridized to the arrays. Hybridizations are incubated overnight at 65° C. in a custom designed chamber that prevents evaporation. Following hybridization, the chip is scanned with a custom confocal laser scanner that will provide an output of the intensity of each spot in the array for both the Cy3 and Cy5 channels. The data are then analyzed with a software package that contains additional extensions. These extensions allow for the integration of a signal across each spot, normalization of the data to a panel of designated housekeeping genes, and statistical calculations to generate a list of genes whose ratios are outliers, or significantly changed by the treatment. In addition to the image analysis software, informatics packages such as Spot-Fire and GeneSpring, both of which are commercially available, are used to allow clustering and analysis of genes in multiple experiments across dose and/or time. cDNA microarray technology, in general, is still being validated as a viable technique for providing quantitative data. While the ratio of red/green provides good qualitative data on the relative level of expression of a gene in one population versus the other, it is not an absolute value of the level of induction/down regulation of that gene. Each pair of samples on the arrays are hybridized in triplicate. Outliers that are consistently induced or suppressed in two of the three hybridization experiments are further validated by a traditional RNA quantitation method, such as Northern blot or RT-PCR.

Each drug is tested at least three times on separate LSC cultures for its effects on growth, differentiation and RNA expression. Cell counts (growth), amount of cells expressing/not expressing and/or exhibiting a particular differentiation marker/characteristic (differentiation) and RNA levels/cDNA microarray data (RNA expression) are averaged for the three or more experiments and the mean and SEM determined. All results are normalized using approximately 15 "house keeping" genes. This allows a quantitative comparison of the effects of the test drugs to control compounds that are not toxic in humans or animals. Statistical comparisons provide information for determining whether a given drug affects LSC gene expression compared to control drugs or non-treated cells and for determining whether a change in RNA in the cells is relevant.

b. Establishing Protein Expression Profiles

The protein expression profiles of the selected anti-cancer drugs are established using Ciphergen's SELDI mass spectroscopy (MS)-TOF system, as described in Example 2. Total cell lysates from harvested LSC cultures are prepared in either 0.1% SDS or Triton-X100 (0.5%) and an equal protein mass is directly applied to protein array chips using manufacturer's protocols. For some situations it may be desirable to add a defined mass of one or more known control peptides as internal calibration and quantification standards to allow more quantitative comparisons between chips and samples. Each chip can analyze two drugs in triplicate. After working out the stringency conditions and experimental replications, on average 6 ProteinChips™ per test compound are used.

The Ciphergen technology allows for the proteins in the sample to be captured, retained and purified directly on the chip. The proteins on the microchip are then analyzed by SELDI. This analysis determines the molecular weight of proteins in the sample. An automatic readout of the molecular weights of the purified proteins in the sample can then be assessed. Typically this system has a CV of less than 20%. The Ciphergen data analysis system normalizes the data to internal reference standards and subtracts the readout of proteins found in control cells from those in drug treated cells. This data analysis reveals protein expression stimulated by the drugs as well as proteins only found in the control cells whose expression is inhibited by the drug. The analysis provides a qualitative readout of protein expression between a control and treated group. Analysis of multiple samples provides an average fold change in protein expression and a relative measure of variability. This can be represented as a mean±SEM which can provide a statistical measure of the protein changes. This analysis is used to determine whether drugs that induce similar forms of toxicity in humans cause similar changes in protein expression in LSCs. Each drug is analyzed on at least 3 separate groups of LSCs.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A first pass method of predicting the type of toxicity of a chemical compound of unknown toxicity, the method comprising the steps of:
   a) contacting an isolated population of mammalian liver stem cells (LSCs) with the chemical compound of unknown toxicity;
   b) creating a molecular profile identifying the alterations in gene expression in the population of LSCs contacted with the chemical composition of unknown toxicity compared to LSCs in contact with culture medium only;
   c) comparing the molecular profile of LSCs contacted with the chemical compound of unknown toxicity to sets of commonly altered RNAs identified from two or more molecular profiles of two or more isolated populations of LSCs wherein each isolated population of LSCs is contacted with one chemical composition of known toxicity, wherein the sets of commonly altered RNAs of the chemical compositions having known liver toxicity have been identified by
      i) contacting each of the isolated populations of mammalian LSCs with one of the chemical compositions having known liver toxicity,
      ii) creating molecular profiles identifying the alterations in gene expression for each of the population of LSCs contacted with each of the chemical compositions of known toxicity compared to LSCs in contact with culture medium only, and
      iii) comparing molecular profiles for known chemical compounds of similar types of toxicity to identify sets of commonly altered RNAs for the chemical compounds of similar type of toxicity; and
   d) predicting toxicity of the chemical composition of unknown toxicity wherein common alterations in gene expressions between the sets of commonly altered RNAs for chemical compounds of similar types of toxicity and the molecular profile from the LSCs contacted with the compound of unknown toxicity indicate the potential correlation of toxicity between the two.

2. The method of claim 1, wherein the level of gene expression is detected by a label directly or indirectly coupled to the nucleic acid.

3. The method of claim 2, wherein the label is selected from the group consisting of a fluorescent, a colorimetric, a radioactive, an enzyme, an enzyme substrate, a nucleoside analog, a magnetic, a glass, a latex bead, a colloidal gold, and an electronic transponder label.

4. The method of claim 2, wherein gene expression is detected by a nucleotide hybridization assay.

5. The method of claim 1, wherein the LSCs are of human origin.

6. The method of claim 5, further wherein the chemical compositions having known liver toxicities are selected from the group consisting of agents that are toxic to cells of one or more reproductive organs, teratogenic agents and carcinogens.

7. The method of claim 5, further wherein the chemical compositions having known liver toxicities are selected from the group consisting of agricultural chemicals, cosmetics, and environmental contaminants.

8. The method of claim 1, wherein the LSCs are of non-human mammalian origin.

9. The method of claim 8, wherein the non-human mammals are rodents.

10. The method of claim 8, further wherein the chemical compositions having known liver toxicities are selected from the group consisting of agents that are toxic to cells of one or more reproductive organs, teratogenic agents and carcinogens.

11. The method of claim 8, further wherein the chemical compositions having known liver toxicities are selected from the group consisting of agricultural chemicals, cosmetics, and environmental contaminants.

12. A method of selecting chemical compositions for liver toxicity preclinical animal studies, said method comprising
   a) predicting the type of toxicity of the chemical composition according to the method of claim 1; and
   b) selecting the chemical compositions of unknown toxicity for preclinical animal studies that have a potential correlation with chemical compounds that are less toxic.

13. The method of claim 12 wherein the predicting is by high throughput screening.

14. The method of claim 1 wherein the molecular profiles of the chemical compositions having known liver toxicity comprise molecular profiles of chemical compositions of two or more different the types of toxicities.

15. A method of generating a library of molecular profiles wherein each molecular profiles is from a population of LSCs contacted with a chemical composition having a known liver toxicity, wherein the molecular profiles are created by the method comprising
   a) contacting two or more isolated populations of LSCs with two or more chemical compositions composition having known liver toxicity, wherein each population of LSCs is contacted with one chemical composition
   b) creating a molecular profile identifying the alterations in gene expression in the population of LSCs contacted with the chemical compositions compared to LSCs in contact with culture medium only
   c) identifying sets of commonly altered RNAs of step b) within molecular profiles from LSCs contacted with chemical compounds of similar type of known toxicity
   d) compiling a library of the molecular profiles; wherein the library is in a computer readable media for use in a computer.

16. The method of claim 15, wherein the library comprises molecular profiles for at least 20 chemical compositions.

17. A systematic method of predicting the type of toxicity of a chemical composition of unknown toxicity, the method comprising the steps of:
   a) contacting an isolated population of mammalian LSCs with the chemical compound of unknown toxicity
   b) creating a molecular profile identifying the alterations in gene expression in the population of LSCs contacted with the chemical compositions compound of unknown toxicity compared to LSCs in contact with culture medium only; and
   c) comparing the molecular profile of step b) with the library of molecular profiles of LSCs contacted with chemical compositions having known liver toxicities generated by the method of claim 15;
   wherein the type of toxicity of the chemical composition of unknown toxicity is predicted by correlating common alterations in molecular profiles from LSCs contacted with the chemical compositions having known liver toxicities and unknown toxicities identified from the comparison of step c).

18. The method of claim 17, wherein the chemical composition of unknown toxicity is a known or an unknown chemical compound.

19. The method of claim 17, further wherein the LSCs are of human origin.

20. The method of claim 19, further wherein the chemical compositions of known toxicities are selected from the group consisting of agents that are toxic to cells of one or more reproductive organs, teratogenic agents and carcinogens.

21. The method of claim 19, further wherein the chemical compositions of known toxicities are selected from the group consisting of agricultural chemicals, cosmetics, and environmental contaminants.

22. The method of claim 17, further wherein the LSCs are of non-human mammalian origin.

23. The method of claim 22, wherein the non-human mammals are rodents.

24. The method of claim 22, further wherein the chemical compositions of known toxicities are selected from the group consisting of agents that are toxic to cells of one or more reproductive organs, teratogenic agents and carcinogens.

25. The method of claim 22, further wherein the chemical compositions of known toxicities are selected from the group consisting of agricultural chemicals, cosmetics, and environmental contaminants.

26. A method of screening chemical compositions for liver toxicity preclinical animal studies, said method comprising
   a) predicting the type of toxicity of the chemical composition according to the method of claim 17; and
   b) selecting the chemical compositions of unknown toxicity for preclinical animal studies that have a potential correlation with chemical compounds that are less toxic.

27. The method of claim 26 wherein the predicting is by high throughput screening.

* * * * *